United States Patent
Jungkamp et al.

(10) Patent No.: US 9,493,405 B2
(45) Date of Patent: Nov. 15, 2016

(54) METHOD FOR PRODUCING LINEAR PENTENENITRILE

(71) Applicant: BASF SE, Ludwigshafen (DE)

(72) Inventors: Tim Jungkamp, Kapellen (BE); Robert Baumann, Mannheim (DE); Michael Bartsch, Neustadt (DE); Gerd Haderlein, Grünstadt (DE); Hermann Luyken, Ludwigshafen (DE); Jens Scheidel, Hirschberg (DE); Tobias Aechtner, Mannheim (DE); Peter Pfab, Shaker Heights, OH (US); Petra Deckert, Bammental (DE); Wolfgang Siegel, Limburgerhof (DE); Peter Bassler, Viernheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/941,167

(22) Filed: Nov. 13, 2015

(65) Prior Publication Data
US 2016/0168082 A1    Jun. 16, 2016

Related U.S. Application Data

(63) Continuation of application No. 10/586,470, filed as application No. PCT/EP2005/000781 on Jan. 27, 2005, now abandoned.

(30) Foreign Application Priority Data

Jan. 29, 2004 (DE) .................. 10-2004-004-671
Sep. 2, 2004 (DE) .................. 10-2004-042-949
Dec. 23, 2004 (DE) .................. 10-2004-063-381

(51) Int. Cl.
*C07C 253/30* (2006.01)
*C07C 253/10* (2006.01)

(52) U.S. Cl.
CPC .......... *C07C 253/30* (2013.01); *C07C 253/10* (2013.01)

(58) Field of Classification Search
CPC ....................... C07C 253/10; C07C 253/30
See application file for complete search history.

(56) References Cited

U.S. PATENT DOCUMENTS

| 3,356,748 | A |   | 12/1967 | Cramer et al. |   |
| 3,536,748 | A | * | 10/1970 | Drinkard, Jr. | .......... B01J 31/185 556/13 |
| 3,852,327 | A |   | 12/1974 | Druliner et al. |   |
| 3,865,865 | A |   | 2/1975 | Musser et al. |   |
| 6,242,633 | B1 | * | 6/2001 | Fischer | ................ B01J 31/1865 558/334 |
| 6,770,770 | B1 | * | 8/2004 | Baumann | ............... B01J 31/185 556/13 |
| 2004/0039221 | A1 | * | 2/2004 | Jungkamp | ............. C07C 253/34 558/463 |

FOREIGN PATENT DOCUMENTS

| DE | 19953058 A1 * | 5/2001 | ............ B01J 31/185 |
| DE | WO 0226698 A1 * | 4/2002 | ........... C07C 253/34 |
| WO | WO-0226698 A1 | 4/2002 | |

OTHER PUBLICATIONS

International Search Report for PCT/EP01/11050 dated Jan. 4, 2002.

* cited by examiner

*Primary Examiner* — Joseph Kosack
(74) *Attorney, Agent, or Firm* — Drinker Biddle & Reath LLP

(57) ABSTRACT

A process is described for preparing 3-pentenenitrile, characterized by the following process steps:

(a) isomerizing a reactant stream which comprises 2-methyl-3-butenenitrile over at least one dissolved or dispersed isomerization catalyst to give a stream 1 which comprises the at least one isomerization catalyst, 2-methyl-3-butenenitrile, 3-pentenenitrile and (Z)-2-methyl-2-butenenitrile, (b) distilling stream 1 to obtain a stream 2 as the top product which comprises 2-methyl-3-butenenitrile, 3-pentenenitrile and (Z)-2-methyl-2-butenenitrile, and a stream 3 as the bottom product which comprises the at least one isomerization catalyst, (c) distilling stream 2 to obtain a stream 4 as the top product which, compared to stream 2, is enriched in (Z)-2-methyl-2-butenenitrile, based on the sum of all pentenenitriles in stream 2, and a stream 5 as the bottom product which, compared to stream 2, is enriched in 3-pentenenitrile and 2-methyl-3-butenenitrile, based on the sum of all pentenenitriles in stream 2, (d) distilling stream 5 to obtain a stream 6 as the bottom product which comprises 3-pentenenitrile and a stream 7 as the top product which comprises 2-methyl-3-butenenitrile.

11 Claims, 9 Drawing Sheets

US 9,493,405 B2

METHOD FOR PRODUCING LINEAR PENTENENITRILE

CROSS-REFERENCE TO RELATED APPLICATIONS

This application is a continuation application, and claims benefit under 35 U.S.C. §120, of U.S. application Ser. No. 10/586,470, filed Jul. 18, 2006, which in turn is a national phase application of PCT/EP2005/000781, filed Jan. 27, 2005, which claims benefit under 35 U.S.C. §119, to German patent application no. 10 2004 004 671.9, filed on Jan. 29, 2004, German patent application no. 10 2004 042 949.9, filed on Sep. 2, 2004, and German patent application no. 10 2004 063 381.9, filed on Dec. 23, 2004, each of the applications of which are incorporated herein by reference in their entirety.

The present invention relates to a process for preparing 3-pentenenitrile by isomerizing streams comprising 2-methyl-3-butenenitrile.

BACKGROUND OF THE INVENTION

In the preparation of adiponitrile, an important intermediate in nylon production, 1,3-butadiene is initially reacted with hydrogen cyanide in the presence of nickel(0) which is stabilized with phosphorus ligands to give pentenenitriles. In addition to the main products of the hydrocyanation, 3-pentenenitrile and 2-methyl-3-butenenitrile, numerous secondary components are also obtained. Examples thereof are 2-pentenenitriles, 2-methyl-2-butenenitriles. $C_9$-nitriles and methylglutaronitrile. 2-methyl-3-butenenitrile is formed in significant amounts. Depending on the catalyst used, the molar ratio of 2-methyl-3-butenenitrile formed to 3-pentenenitrile may be up to 2:1.

In a second hydrocyanation, 3-pentenenitrile is subsequently reacted with hydrogen cyanide to give adiponitrile over the same nickel catalyst with addition of a Lewis acid. For the second hydrocyanation, it is essential that the 3-pentenenitrile is substantially from of 2-methyl-3-butenenitrile. A hydrocyanation of 2-methyl-3-butenenitrile would lead to methylglutaronitrile which constitutes an undesired by-product. Accordingly, in an economic process for preparing adiponitrile, there has to be a separation of 3-pentenenitrile and 2-methyl-3-butenenitrile.

In order to likewise be able to utilize 2-methyl-3-butenenitrile for the preparation of adiponitrile, processes have been proposed for isomerizing 2-methyl-3-butenenitrile to linear pentenenitrile, especially 3-pentenenitrile.

For instance, U.S. Pat. No. 3,676,481 describes the discontinuous, batchwise isomerization of 2-methyl-3-butenenitrile in the presence of Ni(0), a phosphite ligand and certain Lewis acids. After the isomerization, the resulting product mixture is distilled off from the catalyst system. A disadvantage in this process is that of the high residence times during the isomerization, the high thermal stress on the thermally sensitive catalyst during the isomerization and during the subsequent distillation. The high thermal stress on the catalyst leads to undesired degradation of the catalyst.

The German patent application DE 103 11 119.0 to BASF AG, which has an earlier priority date but was unpublished at the priority date of the present application, describes a process for isomerizing 2-methyl-3-butenenitrile to linear pentenenitrile in the presence of a system comprising Ni(0) catalysts and Lewis acids. In this case, a mixture comprising 2-methyl-3-butenenitrile and linear pentenenitrile is withdrawn distillatively from the reaction mixture during the isomerization. A disadvantage in this process is that the product stream withdrawn still contains distinct amounts of unconverted 2-methyl-3-butenenitrile.

It is common to all known processes for isomerizing 2-methyl-3-butenenitrile that 2-methyl-3-butenenitrile cannot be fully converted to 3-pentenenitrile owing to the position of the thermodynamic equilibrium. Unconverted 2-methyl-3-butenenitrile has to be fed to the isomerization step for economic performance of the process. However, in the isomerization of 2-methyl-3-butenenitrile, (Z)-2-methyl-2-butenenitrile is obtained as a by-product and would accumulate in the cycle stream in the case of recycling of 2-methyl-3-butenenitrile, since, in the course of the removal of 3-pentenenitrile from the isomerization product stream by distillation, it would distill over together with the 2-methyl-3-butenenitrile owing to the very similar vapor pressures.

U.S. Pat. No. 3,865,865 describes the removal of 2-methyl-2-butenenitrile from a mixture with 2-methyl-3-butenenitrile. The removal is carried out by treating the mixture of the nitriles with an aqueous solution which consists of sulfite and bisulfite ions. This forms the bisulfite adduct of 2-methyl-2-butenenitrile which transfers to the aqueous phase. The resulting organic phase is depleted to 50% of the original content of 2-methyl-2-butenenitrile. The process of U.S. Pat. No. 3,865,865 is laborious, since a phase separation of an organic from an aqueous phase is required. Furthermore, this separation can only be integrated with difficulty into an overall process for preparing adiponitrile. An additional disadvantage in this process is that the resulting organic phase first has to be fully freed of water before further use in hydrocyanation reactions using nickel (0) catalysts with phosphorus(III) ligands, since the phosphorus(III) ligands are otherwise irreversibly hydrolyzed and thus inactivated. Another disadvantage in this process is that the resulting bisulfite adducts, for the purpose of reuse of the conjugated nitriles, as described in U.S. Pat. No. 3,865,865, can only be dissociated under drastic conditions and only with moderate yield.

DETAILED DESCRIPTION OF THE INVENTION

Figure 9:
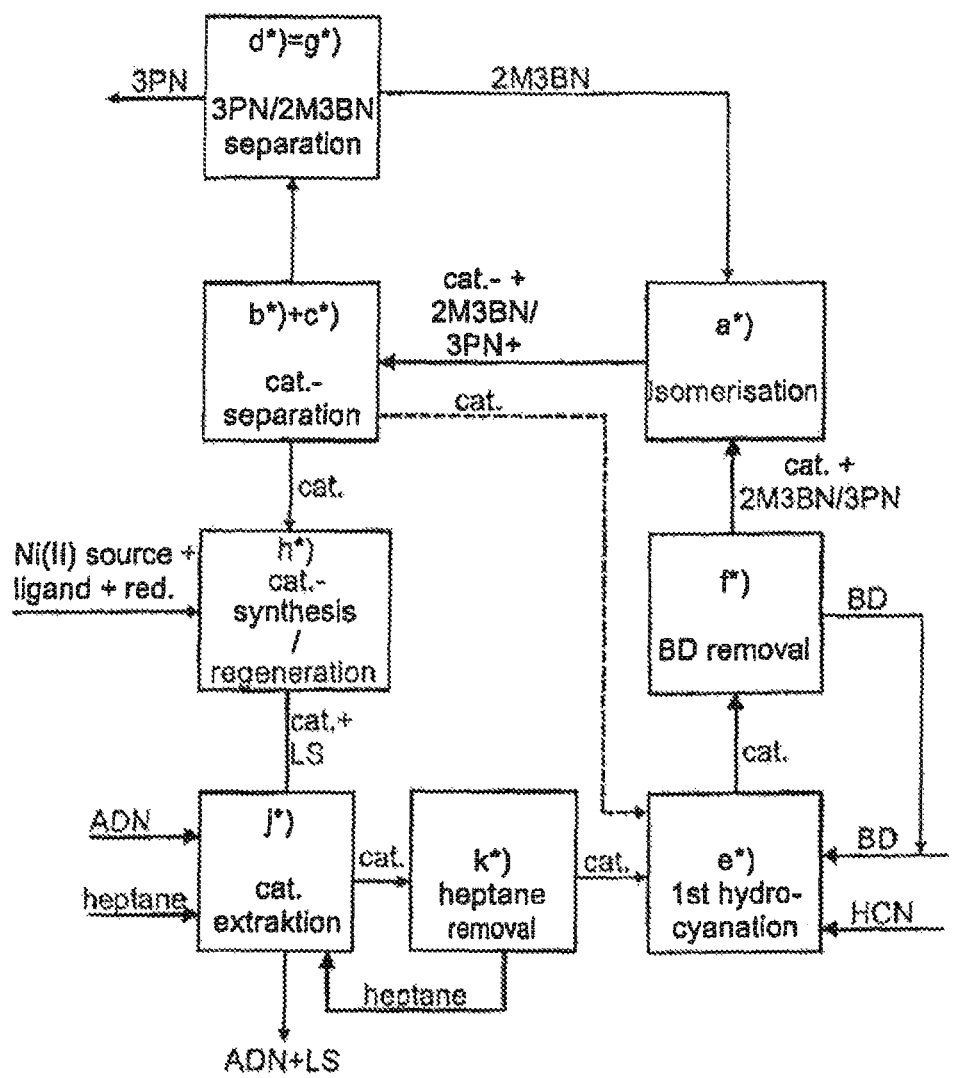
FIG. 9 is a schematic flow diagram of a catalyst circuit without catalyst removal following first hydrocyanation.
Figure 10:
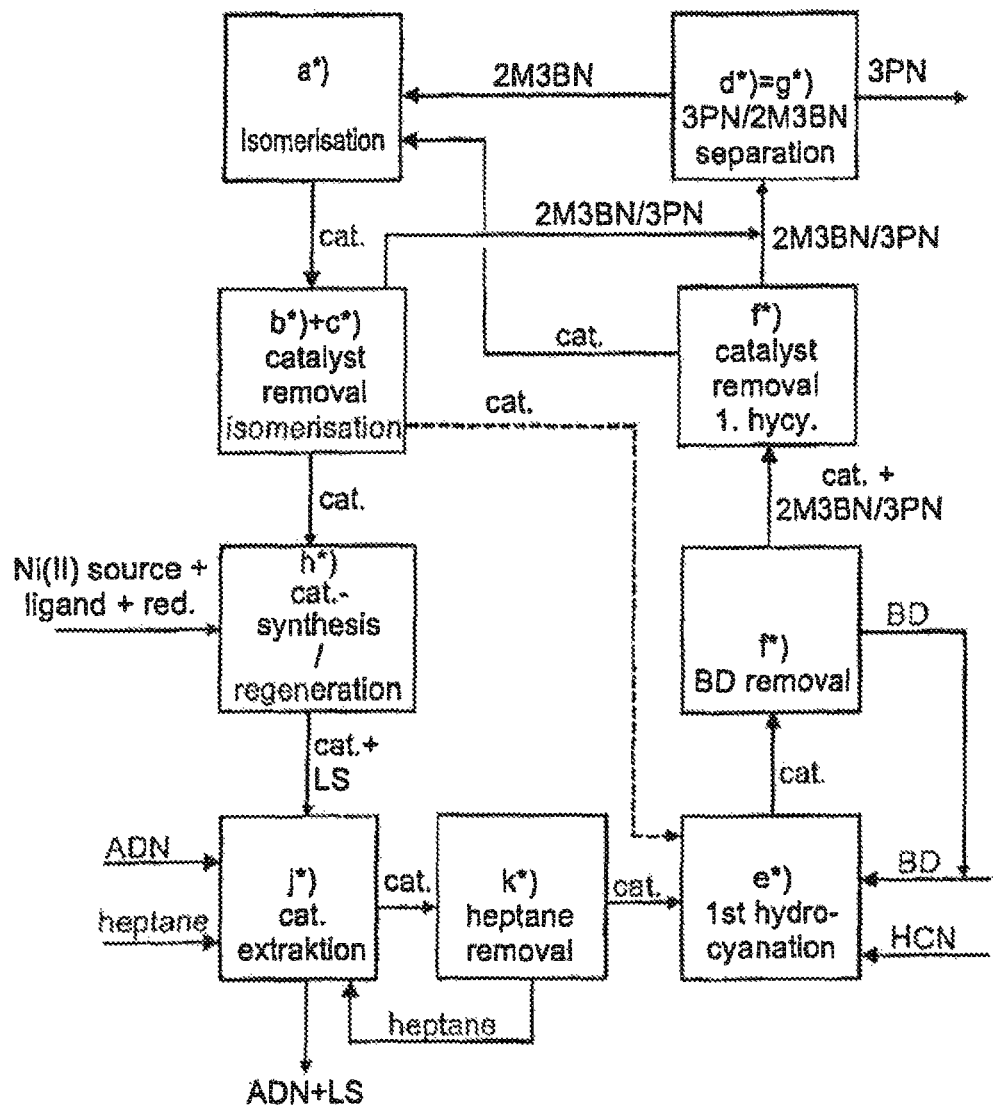
FIG. 10 is schematic flow diagram of a catalyst circuit with catalyst removal following first hydrocyanation.
Figure 11:
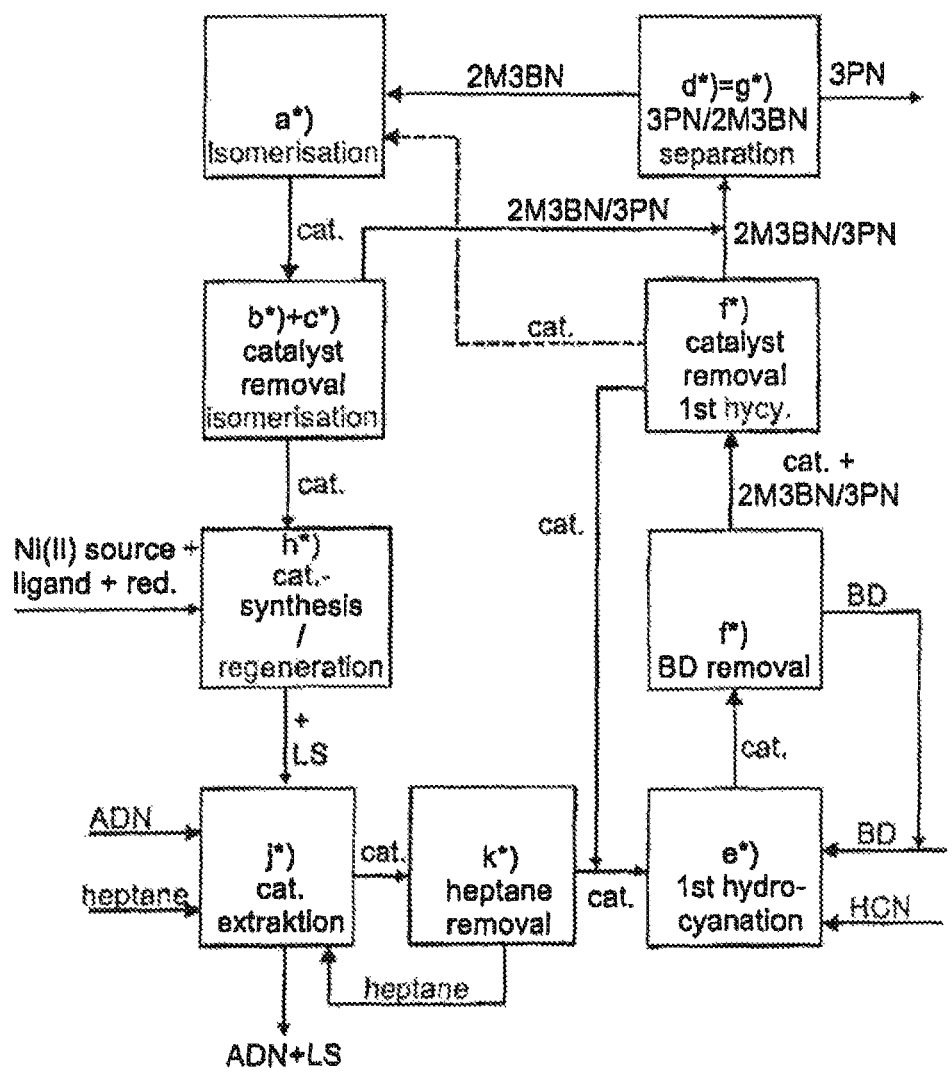
FIG. 11 is another schematic flow diagram of a catalyst circuit with catalyst removal following first hydrocyanation.
Figure 12:
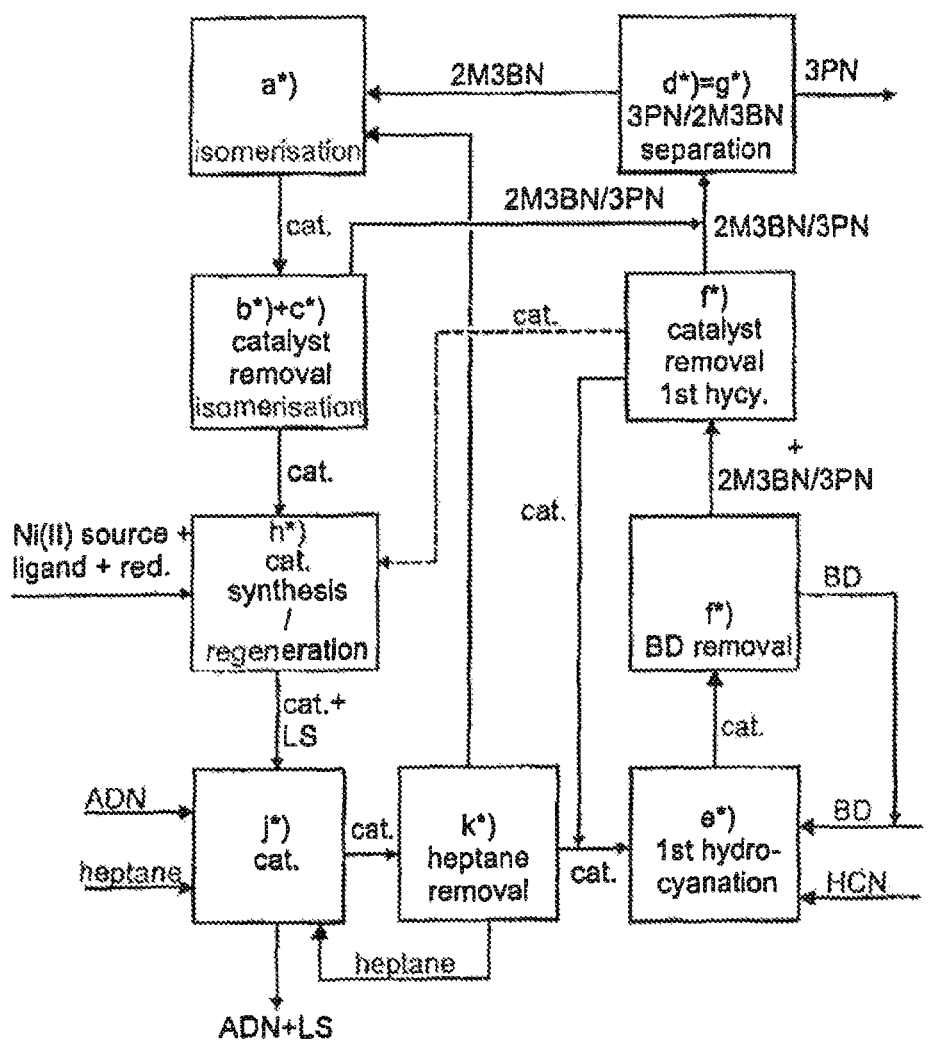
FIG. 12 is another schematic flow diagram of a catalyst circuit with catalyst removal following first hydrocyanation.
Figure 13:
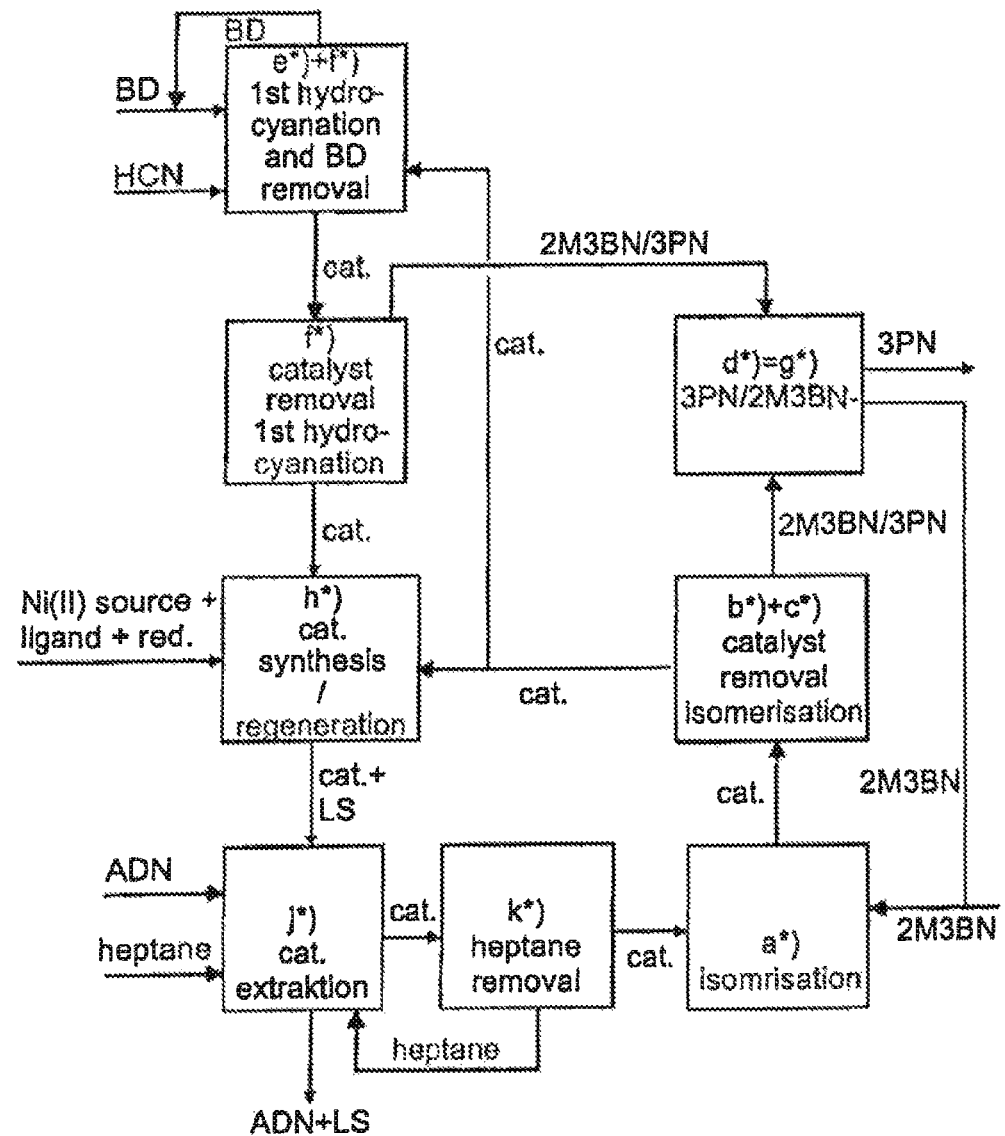
FIG. 13 is another schematic flow diagram of a catalyst circuit with catalyst removal following first hydrocyanation.

FIG. 9 is a schematic flow diagram of a catalyst circuit without catalyst removal following first hydrocyanation. It is thus an object of the present invention to provide a process for preparing 3-pentenenitrile by isomerizing 2-methyl-3-butenenitrile, wherein the catalyst for isomerization can be removed from the reaction mixture in a simple manner and recycled, and both the removal of (Z)-2-methyl-2-butenenitrile from 2-methyl-3-butenenitrile and the recycling of the 2-methyl-3-butenenitrile depleted in (Z)-2-methyl-2-butenenitrile are enabled. The process should preferably be simple and economic to carry out and be incorporable into an overall process for preparing adiponitrile.

This object is achieved in accordance with the invention by a process for preparing 3-pentenenitrile.

Embodiment I

In one embodiment I, the process is characterized by the following process steps:
(a) isomerizing a reactant stream which comprises 2-methyl-3-butenenitrile over at least one dissolved or dispersed isomerization catalyst to give a stream 1 which comprises the at least one isomerization catalyst, 2-methyl-3-butenenitrile, 3-pentenenitrile and (Z)-2-methyl-2-butenenitrile,
(b) distilling stream 1 to obtain a stream 2 as the top product which comprises 2-methyl-3-butenenitrile, 3-pentenenitrile and (Z)-2-methyl-2-butenenitrile, and a stream 3 as the bottom product which comprises the at least one isomerization catalyst,
(c) distilling stream 2 to obtain a stream 4 as the top product which, compared to stream 2, is enriched in (Z)-2-methyl-2-butenenitrile, based on the sum of all pentenenitriles in stream 2, and a stream 5 as the bottom product which, compared to stream 2, is enriched in 3-pentenenitrile and 2-methyl-3-butenenitrile, based on the sum of all pentenenitriles in stream 2,
(d) distilling stream 5 to obtain a stream 6 as the bottom product which comprises 3-pentenenitrile and a stream 7 as the top product which comprises 2-methyl-3-butenenitrile.

Reactant Stream

In process step (a), an isomerization of a reactant stream which comprises 2-methyl-3-butenenitrile takes place over at least one isomerization catalyst.

In a particular embodiment of the process according to the invention, the reactant stream is obtainable by the following process steps:
(e) hydrocyanating 1,3-butadiene over at least one hydrocyanation catalyst using hydrogen cyanide to obtain a stream 8 which comprises the at least one hydrocyanation catalyst, 3-pentenenitrile, 2-methyl-3-butenenitrile, 1,3-butadiene and residues of hydrogen cyanide,
(f) distilling stream 8 once or more than once to obtain a stream 9 which comprises 1,3-butadiene, a stream 10 which comprises the at least one hydrocyanation catalyst, and a stream 11 which comprises 3-pentenenitrile and 2-methyl-3-butenenitrile,
(g) distilling stream 11 to obtain a stream 12 as the bottom product which comprises 3-pentenenitrile, and a stream 13 as the top product which comprises 2-methyl-3-butenenitrile.

In process step (e), the reactant stream is prepared by a hydrocyanation of 1,3-butadiene initially taking place over at least one hydrocyanation catalyst using hydrogen cyanide to obtain a stream 8 which comprises the at least one hydrocyanation catalyst, 3-pentenenitrile, 2-methyl-3-butenenitrile and unconverted 1,3-butadiene.

The hydrocyanation catalyst used is preferably a homogeneous nickel(0) catalyst which is stabilized with phosphorus ligands.

The phosphorus ligands of the nickel(0) complexes and the free phosphorus ligands are preferably selected from mono- or bidentate phosphines, phosphites, phosphinites and phosphonites.

These phosphorus ligands preferably have the formula I

$$P(X^1R^1)(X^2R^2)(X^3R^3) \quad (I)$$

In the context of the present invention, compound I is a single compound or a mixture of different compounds of the aforementioned formula.

According to the invention, $X^1$, $X^2$, $X^3$ each independently are oxygen or a single bond. When all of the $X^1$, $X^2$ and $X^3$ groups are single bonds, compound I is a phosphine of the formula $P(R^1 R^2 R^3)$ with the definitions of $R^1$, $R^2$ and $R^3$ specified in this description.

When two of the $X^1$, $X^2$ and $X^3$ groups are single bonds and one is oxygen, compound I is a phosphinite of the formula $P(OR^1)(R^2)(R^3)$ or $P(R^1)(OR^2)(R^3)$ or $P(R^1)(R^2)(OR^3)$ with the definitions of $R^1$, $R^2$ and $R^3$ specified below.

When one of the $X^1$, $X^2$ and $X^3$ groups is a single bond and two are oxygen, compound I is a phosphonite of the formula $P(OR^1)(OR^2)(R^3)$ or $P(R^1)(OR^2)(OR^3)$ or $P(OR^1)(R^2)(OR^3)$ with the definitions of $R^1$, $R^2$ and $R^3$ specified in this description.

In a preferred embodiment, all $X^1$, $X^2$ and $X^3$ groups should be oxygen, so that compound I is advantageously a phosphite of the formula $P(OR^1)(OR^2)(OR^3)$ with the definitions of $R^1$, $R^2$ and $R^3$ specified below.

According to the invention, $R^1$, $R^2$, $R^3$ are each independently identical or different organic radicals. $R^1$, $R^2$ and $R^3$ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1$, $R^2$ and $R^3$ groups may be bonded together directly, i.e. not solely via the central phosphorus atom. Preference is given to the $R^1$, $R^2$ and $R^3$ groups not being bonded together directly.

In a preferred embodiment, $R^1$, $R^2$ and $R^3$ are radicals selected from the group consisting of phenyl, o-tolyl, m-tolyl and p-tolyl. In a particularly preferred embodiment, a maximum of two of the $R^1$, $R^2$ and $R^3$ groups should be phenyl groups.

In another preferred embodiment, a maximum of two of the $R^1$, $R^2$ and $R^3$ groups should be o-tolyl groups.

Particularly preferred compounds I which may be used are those of the formula Ia

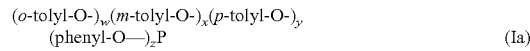

$$(o\text{-tolyl-O-})_w(m\text{-tolyl-O-})_x(p\text{-tolyl-O-})_y(\text{phenyl-O---})_zP \quad (Ia)$$

where w, x, y, z are each a natural number, and the following conditions apply w+x+y+z=3 and w, z≤2, Such compounds Ia are, for example, (p-tolyl-O-)(phenyl-O—)$_2$P, (m-tolyl-O-)(phenyl-O—)$_2$P, (o-tolyl-O-)(phenyl-O—)$_2$P, (p-tolyl-O-)$_2$(phenyl-O—)P, (m-tolyl-O-)$_2$(phenyl-O—)P, (o-tolyl-O-)$_2$(phenyl-O—)P, (m-tolyl-O-)(p-tolyl-O-)(phenyl-O—)P, (o-tolyl-O-)(p-tolyl-O-)(phenyl-O—)P, (o-tolyl-O-)(m-tolyl-O-)(phenyl-O—)P, (p-tolyl-O—)$_3$P, (m-tolyl-O-)(p-tolyl-O—)$_2$P, (o-tolyl-O-)(p-tolyl-O—)$_2$P, (m-tolyl-O-)$_2$(p-tolyl-O—)P, (o-tolyl-O-)$_2$(p-tolyl-O—)P, (o-tolyl-O-)(m-tolyl-O-)(p-tolyl-O—)P, (m-tolyl-O—)$_3$P, (o-tolyl-O-)(m-tolyl-O—)$_2$P (o-tolyl-O-)$_2$(m-tolyl-O—)P or mixtures of such compounds.

Mixtures comprising (m-tolyl-O—)$_3$P, (m-tolyl-O—)$_2$(p-tolyl-O—)P, (m-tolyl-O-)(p-tolyl-O—)$_2$P and (p-tolyl-O—)$_3$ P may be obtained, for example, by reacting a mixture comprising m-cresol and p-cresol, in particular in a molar ratio of 2:1, as obtained in the distillative workup of crude oil, with a phosphorus trihalide, such as phosphorus trichloride.

In another, likewise preferred embodiment, the phosphorus ligands are the phosphites, described in detail in DE-A 199 53 058, of the formula I b:

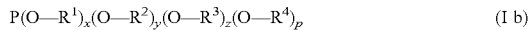

$$P(O—R^1)_x(O—R^2)_y(O—R^3)_z(O—R^4)_p \quad \text{(I b)}$$

where $R^1$: aromatic radical having a $C_1$-$C_{18}$-alkyl subs ent in the o-position to the oxygen atom which joins the phosphorus atom to the aromatic system, or having an aromatic substituent in the o-position to the oxygen atom which joins the phosphorus atom to the aromatic system, or having a fused aromatic system in the o-position to the oxygen atom which joins the phosphorus atom to the aromatic system, $R^2$: aromatic radical having a $C_1$-$C_{18}$-alkyl substituent in the m-position to the oxygen atom which joins the phosphorus atom to the aromatic system, or having an aromatic substituent in the m-position to the oxygen atom which joins the phosphorus atom to the aromatic system, or having a fused aromatic system in the m-position to the oxygen atom which joins the phosphorus atom to the aromatic system, the aromatic radical bearing a hydrogen atom in the o-position to the oxygen atom which joins the phosphorus atom to the aromatic system, $R^3$: aromatic radical having a $C_1$-$C_{18}$-alkyl substituent in the p-position to the oxygen atom which joins the phosphorus atom to the aromatic system, or having an aromatic substituent in the p-position to the oxygen atom which joins the phosphorus atom to the aromatic system, the aromatic radical bearing a hydrogen atom in the o-position to the oxygen atom which joins the phosphorus atom to the aromatic system, $R^4$: aromatic radical which bears substituents other than those defined for $R^1$, $R^2$ and $R^3$ in the o-, m- and p-position to the oxygen atom which joins the phosphorus atom to the aromatic system, the aromatic radical bearing a hydrogen atom in the o-position to the oxygen atom which joins the phosphorus atom to the aromatic system, x: 1 or 2, y,z,p: each independently 0, 1 or 2, with the proviso that x+y+z+p=3.

Preferred phosphites of the formula I b can be taken from DE-A 199 53 058. The $R^1$ radical may advantageously be o-tolyl, o-ethylphenyl, o-n-propylphenyl, o-isopropylphenyl, o-n-butylphenyl, o-sec-butylphenyl, o-tert-butylphenyl, (o-phenyl)phenyl or 1-naphthyl groups.

Preferred $R^2$ radicals are m-tolyl, m-ethylphenyl, m-n-propylphenyl, m-isopropylphenyl, m-n-butylphenyl, m-sec-butylphenyl, m-tert-butylphenyl, (m-phenyl)phenyl or 2-naphthyl groups.

Advantageous $R^3$ radicals are p-tolyl, p-ethylphenyl, p-n-propylphenyl, p-isopropylphenyl, p-n-butylphenyl, p-sec-butylphenyl, p-tert-butylphenyl or (p-phenyl)phenyl groups.

The $R^4$ radical is preferably phenyl. p is preferably zero. For the indices x, y, z and p in compound I b, there are the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Preferred phosphites of the formula I b are those in which p is zero, and $R^1$, $R^2$ and $R^3$ are each independently selected from o-isopropylphenyl, m-tolyl and p-tolyl, and $R^4$ is phenyl.

Particularly preferred phosphites of the formula I b are those in which $R^1$ is the o-isopropylphenyl radical. $R^2$ is the m-tolyl radical and $R^3$ is the p-tolyl radical with the indices specified in the table above; also those in which $R^1$ is the o-tolyl radical, $R^2$ is the m-tolyl radical and $R^3$ is the p-tolyl radical with the indices specified in the table; additionally those in which $R^1$ is the 1-naphthyl radical, $R^2$ is the m-tolyl radical and $R^3$ is the p-tolyl radical with the indices specified in the table; also those in which $R^1$ is the o-tolyl radical. $R^2$ is the 2-naphthyl radical and $R^3$ is the p-tolyl radical with the indices specified in the table; and finally those in which $R^1$ is the o-isopropylphenyl radical. $R^2$ is the 2-naphthyl radical and $R^3$ is the p-tolyl radical with the indices specified in the table; and also mixtures of these phosphites.

Phosphites of the formula I b may be obtained by
a) reacting a phosphorus trihalide with an alcohol selected from the group consisting of $R^1OH$, $R^2OH$, $R^3OH$ and $R^4OH$ or mixtures thereof to obtain a dihalophosphorous monoester,
b) reacting the dihalophosphorous monoester mentioned with an alcohol selected from the group consisting of $R^1OH$, $R^2OH$, $R^3OH$ and $R^4OH$ or mixtures thereof to obtain a monohalophosphorous diester and
c) reacting the monohalophosphorous diester mentioned with an alcohol selected from the group consisting of $R^1OH$, $R^2OH$, $R^3OH$ and $R^4OH$ or mixtures thereof to obtain a phosphite of the formula I b.

The reaction may be carried out in three separate steps. Equally, two of the three steps may be combined, i.e. a) with b) or b) with c). Alternatively, all of steps a), b) and c) may be combined together.

Suitable parameters and amounts of the alcohols selected from the group consisting of $R^1OH$, $R^2OH$, $R^3OH$ and $R^4OH$ or mixtures thereof may be determined readily by a few simple preliminary experiments.

Useful phosphorus trihalides are in principle all phosphorus trihalides, preferably those in which the halide used is Cl, Br, I, in particular Cl, and mixtures thereof. It is also possible to use mixtures of various identically or differently halogen-substituted phosphines as the phosphorus trihalide. Particular preference is given to $PCl_3$. Further details on the reaction conditions in the preparation of the phosphites I b and for the workup can be taken from DE-A 199 53 058.

The phosphites I b may also be used in the form of a mixture of different phosphites I b as a ligand. Such a mixture may be obtained, for example, in the preparation of the phosphites I b.

However, preference is given to the phosphorus ligand being multidentate, in particular bidentate. The ligand used therefore preferably has the formula II

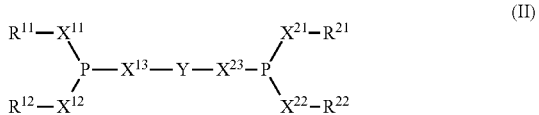

(II)

where
$X^{11}$, $X^{12}$, $X^{13}$, $X^{21}$, $X^{22}$, $X^{23}$ are each independently oxygen or a single bond
$R^{11}$, $R^{12}$ are each independently identical or different, separate or bridged organic radicals
$R^{21}$, $R^{22}$ are each independently identical or different, separate or bridged organic radicals,
Y is a bridging group.

In the context of the present invention, compound II is a single compound or a mixture of different compounds of the aforementioned formula.

In a preferred embodiment, $X^{11}$, $X^{12}$, $X^{13}$, $X^{21}$, $X^{22}$, $X^{23}$ may each be oxygen. In such a case, the bridging group Y is bonded to phosphite groups.

In another preferred embodiment, $X^{11}$ and $X^{12}$ may each be oxygen and $X^{13}$ a single bond, or $X^{11}$ and $X^{13}$ each oxygen and $X^{12}$ a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{21}$ and $X^{22}$ may each be oxygen and $X^{23}$ single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphinite or phosphine, preferably a phosphinite.

In another preferred embodiment, $X^{11}$, $X^{12}$ and $X^{13}$ may each be a single bond, so that the phosphorus atom surrounded by $X^{11}$, $X^{12}$ and $X^{13}$ is the central atom of a phosphine. In such a case, $X^{21}$, $X^{22}$ and $X^{23}$ may each be oxygen, or $X^{21}$, $X^{22}$ and $X^{23}$ may each be a single bond, so that the phosphorus atom surrounded by $X^{21}$, $X^{22}$ and $X^{23}$ may be the central atom of a phosphite or phosphine, preferably a phosphine.

The bridging group Y is advantageously an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol).

The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{21}$ and $R^{22}$ radicals may each independently be the same or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{11}$ and $R^{12}$ radicals may each be separate or bridged. The $R^{21}$ and $R^{22}$ radicals may also each be separate or bridged. The $R^{11}$, $R^{12}$, $R^{21}$ and $R^{22}$ radicals may each be separate, two may be bridged and two separate, or all four may be bridged, in the manner described.

In a particularly preferred embodiment, useful compounds are those of the formula I, II, III, IV and V specified in U.S. Pat. No. 5,723,641. In a particularly preferred embodiment, useful compounds are those of the formula I, II, III, IV, V, VI and VII specified in U.S. Pat. No. 5,512,696, in particular the compounds used there in examples 1 to 31. In a particularly preferred embodiment, useful compounds are those of the formula I, II, III, IV, V, VI, VII, VIII, IX, X, XI, XII, XIII, XIV and XV specified in U.S. Pat. No. 5,821,378, in particular the compounds used there in examples 1 to 73.

In a particularly preferred embodiment, useful compounds are those of the formula I, II, III, IV, V and VI specified in U.S. Pat. No. 5,512,695, in particular the compounds used there in examples 1 to 6. In a particularly preferred embodiment, useful compounds are those of the formula I, II, III, IV, V, VI, VII, VIII, IX, X, XI, XII, XIII and XIV specified in U.S. Pat. No. 5,981,772, in particular the compounds used there in examples 1 to 66.

In a particularly preferred embodiment, useful compounds are those specified in U.S. Pat. No. 6,127,567 and the compounds used there in examples 1 to 29. In a particularly preferred embodiment, useful compounds are those of the formula I, II, III, IV, V, VI, VII, VIII, IX and X specified in U.S. Pat. No. 6,020,516, in particular the compounds used there in examples 1 to 33. In a particularly preferred embodiment, useful compounds are those specified in U.S. Pat. No. 5,959,135, and the compounds used there in examples 1 to 13.

In a particularly preferred embodiment, useful compounds are those of the formula I, II and III specified in U.S. Pat. No. 5,847,191. In a particularly preferred embodiment, useful compounds are those specified in U.S. Pat. No. 5,523,453, in particular the compounds illustrated there in formula 1, 2, 3, 4, 5, 6, 7, 8, 9, 10, 11, 12, 13, 14, 15, 16, 17, 18, 19, 20 and 21. In a particularly preferred embodiment, useful compounds are those specified in WO 01/14392, preferably the compounds illustrated there in formula V, VI, VII, VIII, IX, X, XI, XII, XIII, XIV, XV, XVI, XVII, XXI, XXII, XXIII.

In a particularly preferred embodiment, useful compounds are those specified in WO 98/27054. In a particularly preferred embodiment, useful compounds are those specified in WO 99/13983. In a particularly preferred embodiment, useful compounds are those specified in WO 99/64155.

In a particularly preferred embodiment, useful compounds are those specified in the German patent application DE 100 380 37. In a particularly preferred embodiment, useful compounds are those specified in the German patent application DE 100 460 25. In a particularly preferred embodiment, useful compounds are those specified in the German patent application DE 101 502 85.

In a particularly preferred embodiment, useful compounds are those specified in the German patent application DE 101 502 86. In a particularly preferred embodiment, useful compounds are those specified in the German patent application DE 102 071 65. In a further particularly preferred embodiment of the present invention, useful phosphorus chelate ligands are those specified in US 2003/0100442 A1.

In a further particularly preferred embodiment of the present invention, useful phosphorus chelate ligands are those specified in the German patent application reference number DE 103 50 999.2 of Oct. 30, 2003 which has an earlier priority date but had not been published at the priority date of the present application.

The compounds I, Ia, Ib and II described and their preparation are known per se. Phosphorus ligands used may also be a mixture comprising at least two of the compounds I, Ia, Ib and II.

In a particularly preferred embodiment of the process according to the invention, the phosphorus ligand of the nickel(0) complex and/or the free phosphorus ligand is selected from tritolyl phosphite, bidentate phosphorus chelate ligands and the phosphites of the formula I b

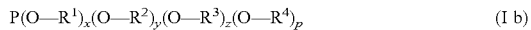

where $R^1$, $R^2$ and $R^3$ are each independently selected from o-isopropylphenyl, m-tolyl and p-tolyl, $R^4$ is phenyl; x is 1 or 2, and y, z, p are each independently 0, 1 or 2 with the proviso that x+y+z+p=3; and mixtures thereof.

Process step (e) may be carried out in any suitable apparatus known to those skilled in the art. Useful apparatus for the reaction is thus customary apparatus, as described, for example, in: Kirk-Othmer, Encyclopedia of Chemical Technology, 4. Ed., Vol. 20, John Wiley & Sons, New York, 1996, pages 1040 to 1055, such as stirred tank reactors, loop reactors, gas circulation reactors, bubble columns or tubular reactors, in each case, if appropriate, with apparatus to remove heat of reaction. The reaction may be carried out in a plurality of, such as two or three, apparatuses.

In a preferred embodiment of the process according to the invention, advantageous reactors have been found to be reactors having backmixing characteristics or batteries of reactors having backmixing characteristics. It has been found that batteries of reactors having backmixing characteristics which are operated in crossflow mode with regard to the metering of hydrogen cyanide are particularly advantageous.

The hydrocyanation may be carried out in the presence or in the absence of a solvent. When a solvent is used, the solvent should be liquid at the given reaction temperature and the given reaction pressure and inert toward the unsaturated compounds and the at least one catalyst. In general, the solvents used are hydrocarbons, for example benzene or xylene, or nitriles, for example acetonitrile or benzonitrile. However, preference is given to using a ligand as the solvent.

The reaction may be carried out in batch mode, continuously or in semibatch operation.

The hydrocyanation reaction may be carried out by charging the apparatus with all reactants. However, it is preferred when the apparatus is filled with the catalyst, the unsaturated organic compound and, if appropriate, the solvent. The gaseous hydrogen cyanide preferably floats over the surface of the reaction mixture or is passed through the reaction mixture. A further procedure for charging the apparatus is the filling of the apparatus with the catalyst, hydrogen cyanide and, if appropriate, the solvent, and slowly metering the unsaturated compound into the reaction mixture. Alternatively, it is also possible that the reactants are introduced into the reactor and the reaction mixture is brought to the reaction temperature at which the hydrogen cyanide is added to the mixture in liquid form. In addition, the hydrogen cyanide may also be added before heating to reaction temperature. The reaction is carried out under conventional hydrocyanation conditions for temperature, atmosphere, reaction time, etc.

Preference is given to carrying out the hydrocyanation continuously in one or more stirred process steps. When a multitude of process steps is used, preference is given to the process steps being connected in series. In this case, the product is transferred from one process step directly into the next process step. The hydrogen cyanide may be fed directly into the first process step or between the individual process steps.

When the process according to the invention is carried out in semibatch operation, preference is given to initially charging the catalyst components and 1,3-butadiene in the reactor, while hydrogen cyanide is metered into the reaction mixture over the reaction time.

The reaction is preferably carried out at absolute pressures of from 0.1 to 500 MPa, more preferably from 0.5 to 50 MPa, in particular from 1 to 5 MPa. The reaction is preferably carried out at temperatures of from 273 to 473 K, more preferably from 313 to 423 K, in particular from 333 to 393 K. Advantageous average mean residence times of the liquid reactor phase have been found to be in the range from 0.001 to 100 hours, preferably from 0.05 to 20 hours, more preferably from 0.1 to 5 hours, in each case per reactor.

In one embodiment, the reaction may be performed in the liquid phase in the presence of a gas phase and, if appropriate, of a solid suspended phase. The starting materials, hydrogen cyanide and 1,3-butadiene, may each be metered in in liquid or gaseous form.

In a further embodiment, the reaction may be carried out in liquid phase, in which case the pressure in the reactor is such that all feedstocks such as 1,3-butadiene, hydrogen cyanide and the at least one catalyst are metered in in liquid form and are in the liquid phase in the reaction mixture. A solid suspended phase may be present in the reaction mixture and may also be metered in together with the at least one catalyst, for example consisting of degradation products of the catalyst system comprising nickel(II) compounds inter alia.

In process step (e), a stream 8 which comprises 3-pentenenitrile, 2-methyl-3-butenenitrile, the at least one catalyst and unconverted 1,3-butadiene is obtained.

Stream 8 which comprises 3-pentenenitrile, 2-methyl-3-butenenitrile, the at least one catalyst and unconverted 1,3-butadiene is subsequently transferred in process step (f) to a distillation apparatus. In this distillation apparatus, stream 8 is distilled once or more than once to obtain a stream 9 which comprises 1,3-butadiene, a stream 10 which comprises the at least one hydrocyanation catalyst, and a stream 11 which comprises 3-pentenenitrile and 2-methyl-3-butenenitrile.

The distillation of process step (f) may be effected in two stages, as described in DE-A-102 004 004 720, process steps (b) and (c). The distillation of process step (f) may also be effected according to DE-A-102 004 004 729, process steps (b) and (c).

The distillation(s) of process step (f) may be carried out in any suitable apparatus known to those skilled in the art.

Suitable apparatus for distillation is described, for example, in: Kirk-Othmer. Encyclopedia of Chemical Technology, 4. Ed., Vol. 8, John Wiley & Sons, New York, 1996, pages 334-348, such as sieve tray columns, bubble-cap tray columns, columns having structured packing or random packing, which may also be operated as dividing wall columns. These distillation units are each equipped with suitable apparatus for evaporating, such as falling-film evaporators, thin-film evaporators, multiphase helical tube evaporators, natural circulation evaporators or forced circulation evaporators, and also with apparatus for condensation of the vapor stream. The individual distillations can each be carried out in a plurality of, such as two or three, apparatuses, advantageously in a single apparatus in each case.

The distillation(s) may additionally each be effected in one stage in the case of a partial evaporation of the feed stream.

The pressure in process step (f) is preferably from 0.001 to 10 bar, more preferably from 0.010 to 1 bar, in particular from 0.02 to 0.5 bar. The distillation(s) is/are carried out in such a way that the temperature(s) in the bottom of the distillation apparatus(es) is/are preferably from 30 to 200° C., more preferably from 50 to 150° C., in particular from 60 to 120° C. The distillation(s) is/are carried out in such a way that the condensation temperatures at the top of the distillation apparatus are preferably from −50 to 150° C., more preferably from −15 to 60° C., in particular from 5 to 45° C. In a particularly preferred embodiment of the process according to the invention, the aforementioned temperature ranges are maintained both at the top and in the bottom of the distillation apparatus(es).

Stream 11 is subsequently subjected to a distillation in a further process step (g). This distillation may be carried out in any suitable apparatus known to those skilled in the art. Suitable apparatus for distillation is described, for example, in: Kirk-Othmer, Encyclopedia of Chemical Technology, 4. Ed., Vol. 8, John Wiley & Sons, New York, 1996, pages 334-348, such as sieve tray columns, bubble-cap tray columns, columns having structured packing or random packing, which may also be operated as dividing wall columns. These distillation units are each equipped with suitable apparatus for evaporating, such as falling-film evaporators, thin-film evaporators, multiphase helical tube evaporators, natural circulation evaporators or forced circulation evaporators, and also with apparatus for condensation of the vapor stream. The individual distillations can each be carried out in a plurality of, such as two or three, apparatuses, advantageously in a single apparatus in each case. The distillation may additionally each be effected in one stage in the case of a partial evaporation of the feed stream.

The pressure in process step (g) is preferably from 0.001 to 100 bar, more preferably from 0.01 to 20 bar, in particular from 0.05 to 2 bar. The distillation is carried out in such a way that the temperature in the bottom of the distillation apparatus is preferably from 30 to 250° C., more preferably from 50 to 200° C., in particular from 60 to 180° C. The distillation is carried out in such a way that the condensation temperature at the top of the distillation apparatus is preferably from −50 to 250° C., more preferably from 0 to 180° C., in particular from 15 to 160° C. In a particularly preferred embodiment of the process according to the invention, the aforementioned temperature ranges are maintained both at the top and in the bottom of the distillation apparatus.

In process step (g), a stream 12 is obtained as the bottom product which comprises 1,3-pentenenitrile, and stream 13 as the top product which comprises 2-methyl-3-butenenitrile. Stream 13 is preferably used as the reactant stream in the process according to the invention for preparing 3-pentenenitrile.

In a further preferred embodiment of the process according to the invention, stream 8 obtained in process step (e) is transferred directly to process step (g). In this process step (g), a stream is then obtained via the bottom and comprises substantially 3-pentenenitrile and the at least one hydrocyanation catalyst. In addition, a stream is obtained overhead which comprises substantially 2-methyl-3-butenenitrile and 1,3-butadiene. This 2-methyl-3-butenenitrile- and 1,3-butadiene-rich stream may likewise be used as the reactant stream in the process according to the invention for preparing 3-pentenenitrile. If this reactant stream is used in the process according to the invention, the content of 2-methyl-3-butenenitrile in this stream is preferably from 10 to 90% by weight, more preferably from 20 to 85% by weight, in particular from 30 to 80% by weight, based in each case on the stream.

Alternatively, it is also possible to deplete stream 8 obtained in process step (e) only in 1,3-butadiene in process step (f). Via the bottom of process step (f) is then obtained a stream 11a which comprises substantially 3-pentenenitrile, 2-methyl-3-butenenitrile and the at least one hydrocyanation catalyst. In that case, this stream 11a is subsequently worked up further in process step (g) with removal of 3-pentenenitrile and the at least one hydrocyanation catalyst on the one hand, and also of 2-methyl-3-butenenitrile on the other. Stream 13a stemming from process step (g) at the top of the distillation comprises substantially 2-methyl-3-butenenitrile. This stream 13a may likewise be used as the reactant stream in the process according to the invention for preparing 3-pentenenitrile.

In a further embodiment, stream 8 from process step (e) is depleted only in 1,3-butadiene in process step (f) and transferred to process step (g), where a stream 12 comprising 3-pentenenitrile and the hydrocyanation catalyst is obtained in the bottom.

In a further embodiment of the present invention, a reactant stream is used which stems from a hydrocyanation of process step (e) and a subsequent workup in process step (f), in which case, if appropriate, only a depletion in 1,3-butadiene is undertaken in process step (f). The stream 11b resulting therefrom is subsequently transferred into process step (a) of the process according to the invention. The hydrocyanation catalyst present in this stream 11b is then preferably used as the at least one isomerization catalyst in process step (a) of the process according to the invention. It is possible to additionally add a suitable Lewis acid, as described, for example, in DE-A-102 004 004 696.

In a further embodiment of the present invention, it is possible that the reactant stream used in the inventive process step (a) corresponds to stream 11 of process step (f), so that a separation of stream 11 in process step (g) is dispensed with.

In a further embodiment of the process according to the invention, the reactant stream used is stream 8 which stems from process step (e). In this case, process steps (f) and (g) are thus dispensed with in the preparation of the reactant stream for the process according to the invention.

Process Step (a)

In process step (a), an isomerization of the reactant stream which comprises 2-methyl-3-butenenitrile takes place over at least one isomerization catalyst. This gives a stream 1 which comprises the isomerization catalyst, unconverted 2-methyl-3-butenenitrile, 3-pentenenitrile and (Z)-2-methyl-2-butenenitrile.

According to the invention, the isomerization is carried out in the presence of a system comprising
a) nickel(0),
b) a compound which contains trivalent phosphorus and complexes nickel(0) as a ligand and, if appropriate,
c) a Lewis acid.

Nickel(0)-containing catalyst systems can be prepared by processes known per se.

The ligands for the isomerization catalyst may be the same phosphorus ligands as used for the hydrocyanation catalyst used in process step (e). The hydrocyanation catalyst may thus be identical to the isomerization catalyst. However, the selection of the ligands for the reactions in process steps (a) and (e) does not necessarily have to be the same.

In addition, the system, if appropriate, comprises a Lewis acid.

In the context of the present invention, a Lewis acid refers to a single Lewis acid or a mixture of a plurality of, such as two, three or four, Lewis acids.

Useful Lewis acids are inorganic or organic metal compounds in which the cation is selected from the group consisting of scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_4$, $TiCL_3$, $ClTi(O-i-propyl)_3$, $MnCl_2$, $ScCl_3$, $AlCl_3$, $(C_8H_{17})AlCl_2$, $(C_8H_{17})_2AlCl$, $(i-C_4H_9)_2AlCl$, $(C_6H_5)_2AlCl$, $(C_6H_5)AlCl_2$, $ReCl_5$, $ZrC_{14}$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$, as described, for example, in U.S. Pat. No. 6,127,567, U.S. Pat. No. 6,171,996 and U.S. Pat. No. 6,380,421. Also useful are metal salts such as $ZnCl_2$, $CoI_2$ and $SnCl_2$, and organometallic compounds such as $RAlCl_2$, $R_2AlCl$, $RSnO_3SCF_3$ and $R_3B$, where R is an alkyl or aryl group, as described, for example, in U.S. Pat. No. 3,496,217, U.S. Pat. No. 3,496,218 and U.S. Pat. No. 4,774,353. According to U.S. Pat. No. 3,773,809, the promoter used may be a metal in cationic form which is selected from the group consisting of zinc, cadmium, beryllium, aluminum, gallium, indium, thallium, titanium, zirconium, hafnium, erbium, germanium, tin, vanadium, niobium, scandium, chromium, molybdenum, tungsten, manganese, rhenium, palladium, thorium, iron and cobalt, preferably zinc, cadmium, titanium, tin, chromium, iron and cobalt, and the anionic moiety of the compound may be selected from the group consisting of halides such as fluoride, chloride, bromide and iodide, anions of lower fatty acids having from 2 to 7 carbon atoms, $HPO_3^{2-}$, $H_3PO^{2-}$, $CF_3COO^-$, $C_7H_{15}OSO_2^-$ or $SO_4^{2-}$. Further suitable promoters, disclosed by U.S. Pat. No. 3,773,809, are borohydrides, organoborohydrides and boric esters of the formula $R_3B$ and $B(OR)_3$, where R is selected from the group consisting of hydrogen, aryl radicals having from 6 to 18 carbon atoms, aryl radicals substituted by alkyl groups having from 1 to 7 carbon atoms and aryl radicals substituted by cyano-substituted alkyl groups having from 1 to 7 carbon atoms, advantageously triphenylboron. Moreover, as described in U.S. Pat. No. 4,874,884, it is possible to use synergistically active combinations of Lewis acids, in order to increase the activity of the catalyst system. Suitable promoters may, for example, be selected from the group consisting of $CdCl_2$, $FeCl_2$, $ZnCl_2$, $B(C_6H_5)_3$ and $(C_6H_5)_3SnX$, where $X=CF_3SO_3$, $CH_3C_6H_4SO_3$ or $(C_6H_5)_3BCN$, and the preferred ratio specified of promoter to nickel is from about 1:16 to about 50:1.

In the context of the present invention, the term Lewis acid also includes the promoters specified in U.S. Pat. No. 3,496,217, U.S. Pat. No. 3,496,218, U.S. Pat. No. 4,774,353, U.S. Pat. No. 4,874,884, U.S. Pat. No. 6,127,567, U.S. Pat. No. 6,171,996 and U.S. Pat. No. 6,380,421.

Particularly preferred Lewis acids among those mentioned are in particular metal salts, more preferably metal halides, such as fluorides, chlorides, bromides, iodides, in particular chlorides, of which particular preference is given to zinc chloride, iron(II) chloride and iron(III) chloride.

The isomerization may be carried out in the presence of a liquid diluent,
  for example a hydrocarbon such as hexane, heptane, octane, cyclohexane, methylcyclohexane, benzene, decahydronaphthalene
  for example an ether such as diethyl ether, tetrahydrofuran, dioxane, glycol dimethyl ether, anisole,
  for example an ester such as ethyl acetate, methyl benzoate, or
  for example a nitrile such as acetonitrile, benzonitrile, or mixtures of such diluents.

In a particularly preferred embodiment, a useful isomerization is in the absence of such a liquid diluent.

Moreover, it has been found to be advantageous when the isomerization in process step (a) is carried out in an unoxidizing atmosphere, for example under a protective gas atmosphere composed of nitrogen or a noble gas such as argon.

Process step (a) may be carried out in any suitable apparatus known to those skilled in the art. Useful apparatus for this reaction is customary apparatus as described, for example, in: Kirk-Othmer. Encyclopedia of Chemical Technology, 4. Ed., Vol. 20, John Wiley & Sons, New York, 1996, pages 1040 to 1055, such as stirred tank reactors, loop reactors, gas circulation reactors, bubble column reactors or tubular reactors. The reaction may be carried out in a plurality of, such as two or three, apparatuses.

In a preferred embodiment of the process according to the invention, the isomerization is carried out in a compartmented tubular reactor.

In a further preferred embodiment of the process according to the invention, the isomerization is carried out in at least two reactors connected in series, in which case the first reactor has substantially stirred tank characteristics and the second reactor is designed in such a way that it has substantially tubular characteristics.

In a particularly preferred embodiment of the process according to the invention, the isomerization is carried out in a reactor, the reactor having the characteristics of a stirred tank battery which corresponds to from 2 to 20 stirred tanks, in particular from 3 to 10 stirred tanks.

In one embodiment of the process according to the invention, the reaction may be carried out in one distillation apparatus, in which case the isomerization reaction takes place at least in the bottom region of the distillation apparatus. Any distillation apparatus known to those skilled in the art is suitable, as described, for example, in: Kirk-Othmer, Encyclopedia of Chemical Technology, 4. Ed., Vol. 8, John Wiley & Sons, New York, 1996, pages 334-348, such as sieve tray columns, bubble-cap tray columns, columns having structured packing or random packing, which may also be operated as dividing wall columns. These distillation units are each equipped with suitable apparatus for evaporation, such as falling-film evaporators, thin-film evaporators, multiphase helical tube evaporators, natural circulation evaporators or forced circulation evaporators, and also with apparatus for condensing vapor stream. The distillation with simultaneous reaction can be carried out in a plurality of, such as two or three, apparatuses, advantageously in a single apparatus. The distillation may additionally be effected in one stage in the case of a partial evaporation of the feed stream.

Process step (a) of the process according to the invention is preferably carried out at an absolute pressure of from 0.1 mbar to 100 bar, more preferably from 1 mbar to 16 bar, in particular from 10 mbar to 6 bar. The temperature in process step (a) is preferably from 25 to 250° C., more preferably from 30 to 180° C., in particular from 40 to 140° C.

The composition of the stream withdrawn, with regard to the molar ratio of 2-methyl-3-butenenitrile to linear pentenenitrile and thus the degree of conversion of 2-methyl-3-butenenitrile used, may be adjusted, depending on the composition of the feed stream, in a technically simple manner by the temperature, the catalyst concentration, the residence time and the configuration of the reactor. In a preferred embodiment of the process according to the invention, the degree of conversion is adjusted with the aid of these measures to values in the range from 10 to 99%, more preferably from 30 to 95%, in particular from 60 to 90%.

Process Step (b)

In process step (b), the stream 1 obtained in process step (a) is distilled. This gives a stream 2 which comprises 2-methyl-3-butenenitrile, 3-pentenenitrile and (Z)-2-methyl-2-butenenitrile as the top product. In addition, a stream 3 is obtained in process step (b) as the bottom product which comprises the at least one isomerization catalyst.

Process step (b) of the process according to the invention may be carried out in any suitable distillation apparatus known to those skilled in the art. Suitable apparatus for distillation is described, for example, in: Kirk-Othmer. Encyclopedia of Chemical Technology, 4. Ed., Vol. 8, John Wiley & Sons, New York, 1996, pages 334-348, such as sieve tray columns, bubble-cap trays columns, columns having structured packing or random packing, which may also be operated as dividing wall columns. These distillation units are each equipped with suitable apparatus for evaporating, such as falling-film evaporators, thin-film evaporators, multiphase helical tube evaporators, natural circulation evaporators or forced circulation evaporators, and also with apparatus for condensation of the vapor stream. The distillation can be carried out in a plurality of, such as two or three, apparatuses, advantageously in a single apparatus. The distillation may additionally be effected in one stage in the case of a partial evaporation of the feed stream.

Process step (b) of the process according to the invention is preferably carried out at an absolute pressure of from 0.1 mbar to 100 bar, more preferably from 1 mbar to 6 bar, in particular from 10 mbar to 500 mbar. The distillation is carried out in such a way that the temperature in the bottom of the distillation apparatus is preferably from 25 to 250° C., more preferably from 40 to 180° C., in particular from 60 to 140° C. The distillation is carried out in such a way that the temperature at the top of the distillation apparatus is preferably from −15 to 200° C., more preferably from 5 to 150° C., in particular from 10 to 100° C. In a particularly preferred embodiment of the process according to the invention, the aforementioned temperature ranges are maintained both at the top and in the bottom of the distillation apparatus.

In a particularly preferred embodiment of the present invention, the distillation, carried out in process step (b), of stream 1 takes place under pressure and temperature conditions under which the isomerization catalyst present in the mixture is less active than in process step (a) or is inactive.

In a preferred embodiment of the present invention, stream 3, obtained in process step (b), which comprises the at least one isomerization catalyst is recycled at least partly into process step (a).

In a further embodiment of the process according to the invention, process steps (a) and (b) take place in the same apparatus. It is also possible that stream 3 which comprises the at least one isomerization catalyst is not withdrawn from process step (b) and resides in the common apparatus of process steps (a) and (b).

Alternatively, it is also possible that stream 3, stemming from process step (b), which comprises the at least one isomerization catalyst is used at least partly to prepare the reactant stream used in accordance with the invention in process step (e). In process step (e), this at least one isomerization catalyst then functions as a hydrocyanation catalyst.

Process Step (c)

In process step (c), a distillation of stream 2 takes place. This gives a stream 4 as the top product which, compared to stream 2, is enriched in (Z)-2-methyl-2-butenenitrile in relation to the sum of all pentenenitriles present in stream 2. In addition, a stream 5 is obtained as the bottom product which, compared to stream 2, is depleted in (Z)-2-methyl-2-butenenitrile in relation to the sum of all pentenenitriles present in stream 2.

Process step (c) may be carried out in any suitable apparatus known to those skilled in the art. Suitable apparatus for distillation is described, for example, in: Kirk-Othmer, Encyclopedia of Chemical Technology, 4. Ed., Vol. 8, John Wiley & Sons, New York, 1996, pages 334-348, such as sieve tray columns, bubble-cap tray columns, columns having structured packing or random packing, which may also be operated as dividing wall columns. These distillation units are each equipped with suitable apparatus for evaporating, such as falling-film evaporators, thin-film evaporators, multiphase helical tube evaporators, natural circulation evaporators or forced circulation evaporators, and also with apparatus for condensation of the vapor stream. The distillation can be carried out in a plurality of, such as two or three, apparatuses, advantageously in a single apparatus. The distillation may additionally be effected in one stage in the case of a partial evaporation of the feed stream.

Process step (c) of the process according to the invention is preferably carried out at an absolute pressure of from 0.1 mbar to 100 bar, more preferably from 1 mbar to 6 bar, in particular from 10 mbar to 500 mbar. The distillation is carried out in such a way that the temperature in the bottom of the distillation apparatus is preferably from 25 to 250° C., more preferably from 40 to 180° C., in particular from 60 to 140° C. The distillation is carried out in such a way that the temperature at the top of the distillation apparatus is preferably from −15 to 200° C., more preferably from 5 to 150° C., in particular from 10 to 100° C. In a particularly preferred embodiment of the process according to the invention, the aforementioned temperature ranges are maintained both at the top and in the bottom of the distillation apparatus.

In a particularly preferred embodiment of the process according to the invention, process steps (b) and (c) are carried out together in one distillation apparatus, in which case stream 3 which comprises the at least one isomerization catalyst is obtained as the bottom product, stream 4 which comprises (Z)-2-methyl-2-butenenitrile as the top product, and stream 5 which comprises 3-pentenenitrile and 2-methyl-3-butenenitrile at a side draw of the column.

In a further preferred embodiment of the process according to the invention, process steps (a), (b) and (c) are carried out together in one distillation apparatus. In this case, stream 4 which comprises (Z)-2-methyl-2-butenenitrile is obtained as the top product. Stream 5 which comprises 3-pentenenitrile and 2-methyl-3-butenenitrile is obtained at a side draw of the distillation column. In this embodiment, the isomerization catalyst remains preferably in the bottom of the distillation column.

Process Step (d)

Stream 5, obtained in process step (c), which comprises 3-pentenenitrile and 2-methyl-3-butenenitrile is subsequently transferred to a further distillation apparatus. In this distillation apparatus, stream 5 is separated into a 3-pentenenitrile stream which is withdrawn as the bottom product, and a 2-methyl-3-butenenitrile stream which is withdrawn at the top.

Process step (d) may be carried out in any suitable apparatus known to those skilled in the art. Suitable apparatus for distillation is described, for example, in: Kirk-Othmer, Encyclopedia of Chemical Technology, 4. Ed., Vol. 8, John Wiley & Sons, New York, 1996, pages 334-348, such as sieve tray columns, bubble-cap tray columns, columns having structured packing or random packing, which may also be operated as dividing wall columns. These distillation units are each equipped with suitable apparatus for evaporating, such as falling-film evaporators, thin-film evaporators, multiphase helical tube evaporators, natural circulation evaporators or forced circulation evaporators, and also with apparatus for condensation of the vapor stream. The distillation can be carried out in a plurality of, such as two or three, apparatuses, advantageously in a single apparatus. The distillation may additionally be effected in one stage in the case of a partial evaporation of the feed stream.

The absolute pressure in process step (d) is preferably from 0.001 to 100 bar, more preferably from 0.01 to 20 bar, in particular from 0.05 to 2 bar. The distillation is carried out in such a way that the temperature in the bottom of the distillation apparatus is preferably from 30 to 250° C., more preferably from 50 to 200° C., in particular from 60 to 180° C. The distillation is carried out in such a way that the condensation temperature at the top of the distillation apparatus is preferably from −50 to 250° C., more preferably from 0 to 180° C., in particular from 15 to 160° C.

In a particularly preferred embodiment of the process according to the invention, the aforementioned temperature ranges are maintained both at the top and in the bottom of the distillation apparatus.

In a particularly preferred embodiment of the process according to the invention, process step (d) and process step (g) are carried out in the same distillation apparatus. In this case, streams 6 and 12, and also 7 and 13, coincide. In addition, in this preferred embodiment, stream 5 is conducted directly into the common apparatus of process steps (d) and (g). In this case, the feed points of streams 5 and 11, in the case of a distillation column as the distillation apparatus, may be the same or different.

In a further embodiment of the process according to the invention, process steps (c) and (g) are carried out in a common distillation column, in which case process step (d) is dispensed with, stream 2 from process step (b) and stream 11 from process step (f) are conducted into process step (g), and, in process step (g), stream 4 is obtained as the top product comprising (Z)-2-methyl-2-butenenitrile, stream 12 as the bottom product comprising 3-pentenenitrile and stream 13 as a side draw stream comprising 2-methyl-3-butenenitrile.

In the process according to the invention of embodiment I, it is possible that stream 2 is recycled directly into process step (g) and the reactant stream is conducted directly into process step (c), in which case a stream 5a from process step (c) is recycled into the isomerization of process step (a).

Alternatively, it is also possible to recycle stream 2 directly into process step (g) and conduct the reactant stream into process step (c), in which case stream 5 from process step (c) is recycled into process step (f).

Alternatively, it is also possible that stream 2 is recycled directly into process step (g) and the reactant stream is conducted into process step (c), and stream 5 from process step (c) is recycled into process step (e).

Embodiment II

The present invention further provides a process for preparing 3-pentenenitrile according to an embodiment II, which is characterized by the following process steps:

(a') isomerizing a reactant stream which comprises 2-methyl-3-butenenitrile over at least one dissolved or dispersed isomerization catalyst to give a stream 1' which comprises 3-pentenenitrile, 2-methyl-3-butenenitrile, the at least one isomerization catalyst and (Z)-2-methyl-2-butenenitrile, (b') distilling stream 1' to obtain a stream 2' which comprises (Z)-2-methyl-2-butenenitrile, 2-methyl-3-butenenitrile, and recycling it into the isomerization step (a'), a stream 3' as the bottom product which comprises the at least one isomerization catalyst and recycling it into the isomerization step (a'), and a stream 4' which comprises 3-pentenenitrile at a side draw of the distillation column.

The reactant stream which is used in process step (a') of the process according to the invention according to embodiment II may be obtained by the above-described process for preparing the reactant stream for the process according to the invention according to embodiment I.

For process step (a') according to embodiment II, the same conditions apply as for process step (a) according to embodiment I, especially with regard to the catalyst complex used and the free ligand.

The absolute pressure in process step (b') is preferably from 0.001 to 100 bar, more preferably from 0.01 to 20 bar, in particular from 0.1 to 2 bar. The distillation is carried out in such a way that the temperature in the bottom of the distillation apparatus is preferably from 25 to 250° C., more preferably from 40 to 180° C., in particular from 60 to 140° C. The distillation is carried out in such a way that the condensation temperature at the top of the distillation apparatus is preferably from −50 to 250° C., more preferably from 0 to 150° C., in particular from 10 to 100° C.

A partial discharge of stream 2' is in some cases appropriate in order to prevent accumulation of (Z)-2-methyl-2-butenenitrile. The residual stream is recycled in step (a').

In one variant of the present process according to embodiment II, the reactant stream is conducted into process step (b') instead of into process step (a).

Stream 2' which leaves process step (b') in the process according to the invention according to embodiment II may, if appropriate, in a further optional process step (c') be subjected to a distillation. This preferably forms a (Z)-2-methyl-2-butenenitrile-enriched stream 5' and a (Z)-2-methyl-2-butenenitrile-depleted stream 6', and stream 5' is preferably recycled into process step (a').

Process step (c') to be carried out if appropriate may also be carried out in the apparatus of process step (a'), in which case a distillation apparatus is then used in process step (a') in whose bottom the isomerization reaction takes place, stream 1' is drawn off via the bottom of the distillation apparatus, and the (Z)-2-methyl-2-butenenitrile-rich stream 6' is drawn off via the top of the distillation apparatus.

According to the invention, in the processes according to embodiment I and II, 3-pentenenitrile is obtained. In the context of the present invention, the term 3-pentenenitrile refers to a single isomer of 3-pentenenitrile or a mixture of two, three, four or five different such isomers. Isomers include cis-2-pentenenitrile, trans-2-pentenenitrile, cis-3-pentenenitrile, trans-3-pentenenitrile, 4-pentenenitrile or mixtures thereof, preferably cis-3-pentenenitrile, trans-3-pentenenitrile, 4-pentenenitrile or mixtures thereof, which are referred to in the context of the present invention, both in each case individually and as a mixture, as 3-pentenenitrile.

The process according to the invention is associated with advantages. For instance, in an integrated process for preparing adiponitrile, for example, the recycling of unconverted 2-methyl-3-butenenitrile from the isomerization is economically necessary, because the degree of conversion of 2-methyl-3-butenenitrile to 3-pentenenitrile is restricted by the thermodynamic equilibrium. The recycling entails the removal of (Z)-2-methyl-2-butenenitrile which accumulates in the 2-methyl-3-butenenitrile circuit. In the process according to the invention, the removal is effected by distillation to separate 2-methyl-3-butenenitrile and (Z)-2-methyl-2-butenenitrile preferably only after step (a) has been carried out, in step (c), in order to minimize losses of products of value in a controlled manner.

Figure 1:
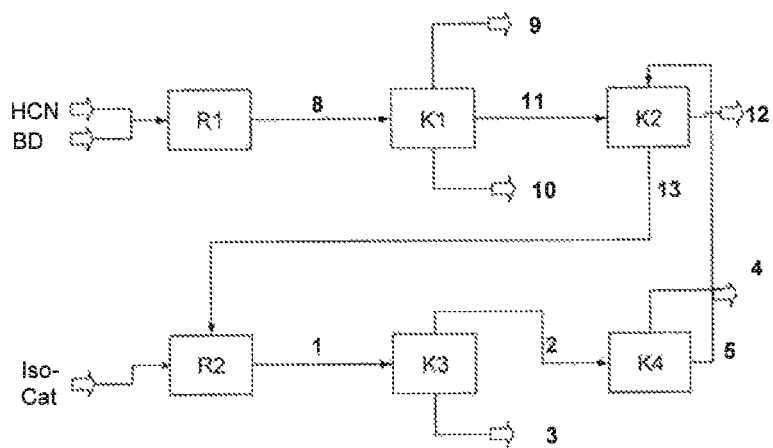
FIG. 1 is a schematic representation of an embodiment of the invention.

The process according to the invention according to a preferred version of embodiment 1 is illustrated in detail with reference to FIG. 1:

In a reactor R1, hydrogen cyanide and 1,3-butadiene are fed in in the presence of a nickel(0) catalyst. In the reactor, hydrocyanation takes place to form a stream 8. This stream 8 comprises 3-pentenenitrile, 2-methyl-3-butenenitrile, the hydrocyanation catalyst and unconverted 1,3-butadiene. Subsequently, stream 8 is transferred to a distillation column K1 in which 1,3-butadiene (stream 9) is removed from stream 8 overhead. In the bottom of the distillation column K1, a stream 10 is obtained which comprises the hydrocyanation catalyst. At the side draw of the distillation column K1, a stream 11 is obtained which comprises 3-pentenenitrile and 2-methyl-3-butenenitrile. This stream 11 is subsequently transferred to a distillation column K2.

In the distillation column K2, stream 11 is separated into a stream 12 which comprises 3-pentenenitrile, and a stream 13 which comprises 2-methyl-3-butenenitrile.

Stream 13 is subsequently transferred to an isomerization apparatus R2. In this isomerization apparatus R2, the 2-methyl-3-butenenitrile which is present in stream 13 is isomerized over an isomerization catalyst. The stream 1 stemming from this isomerization comprises 3-pentenenitrile, 2-methyl-3-butenenitrile, (Z)-2-methyl-2-butenenitrile, and also the isomerization catalyst.

This stream 1 is subsequently separated in a distillation apparatus K3. This forms stream 3 which comprises the isomerization catalyst (bottoms). At the top of the distillation apparatus K3, stream 2 is withdrawn. This stream 2 comprises 3-pentenenitrile, (Z)-2-methyl-2-butenenitrile and 2-methyl-3-butenenitrile. This stream 2 is subsequently transferred to a distillation column K4.

In this distillation column K4, stream 2 is separated into (Z)-2-methyl-2-butenenitrile which has been formed during the isomerization (stream 4). In addition, stream 5 is obtained in the bottom of the distillation column K4 and comprises 3-pentene nitrile and 2-methyl-3-butenenitrile.

This stream 5 is transferred to the distillation column K2, and the 3-pentenenitrile is obtained from stream 5 in the distillation column.

Streams 9 and 10 may be partly or fully recycled into the reactor R1, or not recycled into it at all. The same applies to stream 3 in the direction of reactor R2. These variants are not shown in FIG. 1.

The process according to the invention according to a preferred version of embodiment II is illustrated in detail with reference to FIG. 2:

In a reactor R1, hydrogen cyanide and 1,3-butadiene are fed in in the presence of a nickel(0) catalyst. In the reactor, hydrocyanation takes place to form a stream 8. This stream 8 comprises 3-pentenenitrile, 2-methyl-3-butenenitrile, the hydrocyanation catalyst and unconverted 1,3-butadiene. Subsequently, stream 8 is transferred to a distillation column K1 in which 1,3-butadiene (stream 9) is removed from stream 8 overhead. In the bottom of the distillation column K1, a stream 10 is obtained which comprises the hydrocyanation catalyst. At the side draw of the distillation column K1, a stream 11 is obtained which comprises 3-pentenenitrile and 2-methyl-3-butenenitrile. This stream 11 is subsequently transferred to an isomerization apparatus R2.

In the isomerization apparatus R2, isomerization catalyst (stream 3') and 2-methyl-3-butenenitrile (stream 2'), each stemming from the distillation column K2, are additionally introduced. In the isomerization apparatus R2, an isomerization takes place. The stream 1' resulting therefrom is subsequently transferred to the distillation apparatus K2 in which stream 1' is separated into a stream 2' (2-methyl-3-butenenitrile) which is recycled into R2, a stream 3' (isomerization catalyst) which is recycled into R2, and into a stream 4' which comprises 3-pentenenitrile.

Feeding of a stream comprising isomerization catalyst to R2 allows any necessary discharges from stream 3' to be compensated, so that the Ni(0) content in R2 remains constant.

Figure 2:
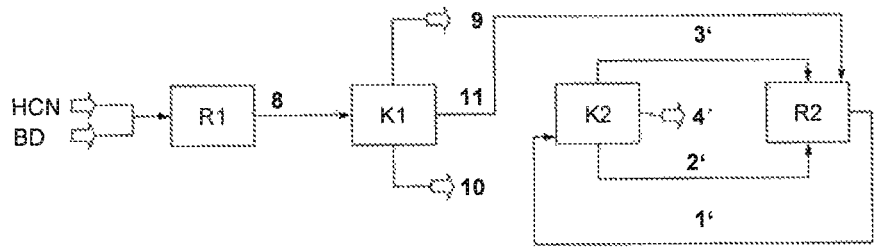
FIG. 2 is a schematic representation of another embodiment of the invention.

Streams 9 and 10 may be recycled fully or partly into the reactor R1, or not recycled into it at all:

These recycling and discharge variants are not shown in FIG. 2.

The present invention is illustrated in detail with reference to the examples detailed hereinbelow.

WORKING EXAMPLES

In the examples, the following abbreviations are used:
hydrogen cyanide: hydrogen cyanide
T3PN: trans-3-pentenenitrile
C3PN: cis-3-pentenenitrile
4PN: 4-pentenenitrile
E2M2BN: (E)-2-methyl-2-butenenitrile
T2PN: trans-2-pentenenitrile
C2PN: cis-2-pentenenitrile
ADN: adiponitrile
MGN: methylglutaronitrile
VAN: valeronitrile
VCH: 4-vinylcyclohexene
BD: 1,3-butadiene
TBP: tert-butylpyrocatechol
C2BU: cis-2-butene In the examples, the process steps are reported in a chronological sequence and thus deviate from the designation in the description and in the claims. Data in 96 or ppm which is not characterized in detail are % by weight and ppm by weight respectively.

Example 1

Figure 3:
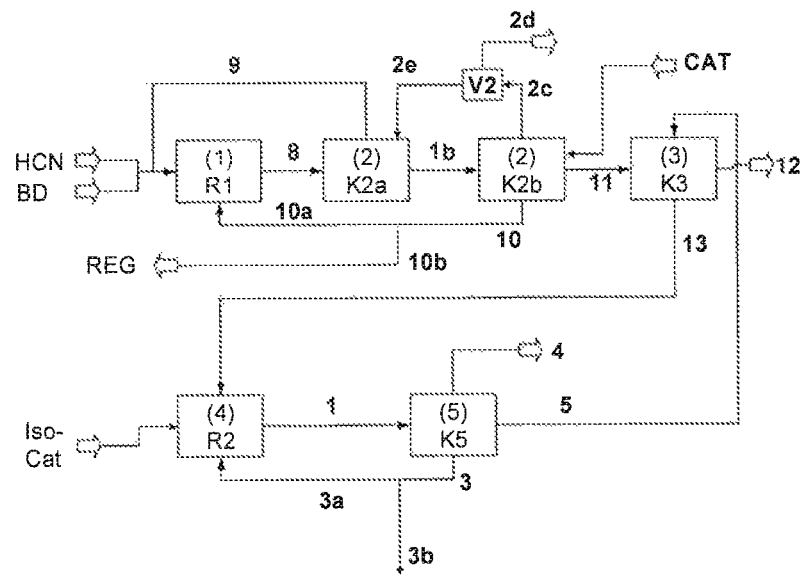
FIG. 3 is a schematic representation of Example 1.

Example 1 is illustrated with reference to FIG. 3.

In Example 1, a catalyst system based on nickel(0) complexes with a mixture of ligands is used for the hydrocyanation of butadiene. The ligand mixture for the hydrocyanation contains approx. 60 mol % of tri(m/p-tolyl) phosphite and 40 mol % of the chelate phosphonite 1:

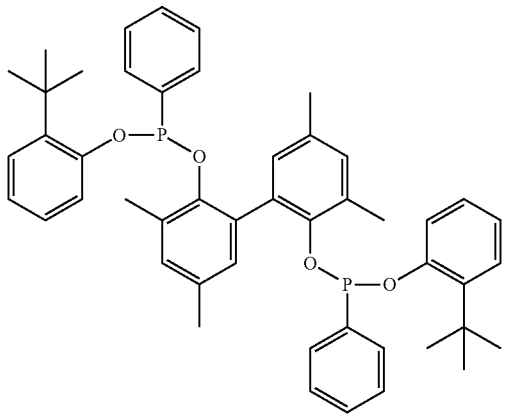

In a step (1), the following streams are conducted into a loop reactor R1 of capacity 25 l which is equipped with a nozzle, impulse exchange tube, external pump circulation and in a heat exchanger disposed in the pump circulation system for removing the energy of reaction and is heated to 357 K:
(1) 10 kg/h of liquid unstabilized hydrogen cyanide freed of water by distillation,
(2) 22 kg/h of commercial BD containing 0.25% C2BU which have been treated by contact with alumina in order to remove water and TBP stabilizer,
(3) 8 kg/h of recycled BD from K2a in step (2) (stream 9), so that the entire BD feed to the reactor R1 which is obtained is a stream of 30 kg/h containing 90% BD, 5% C2BU and 5% 1-butene,
(4) 21 kg/h of nickel(0) catalyst solution, obtained as described below in this example, as stream 10a from column K2b The stream 8 withdrawn from the reactor R1 (63 kg/h) contains a total of 11% BD and C2BU, corresponding to a conversion of 79% BD, and also a total of 63% pentenenitriles, 31% T3PN, 29% 2M3BN and small amounts of Z2M2BN and E2M2BN, and further pentenenitrile isomers (T2PN, C2PN, C3PN, 4PN), and also the catalyst constituents and catalyst degradation products and MGN.

Stream 8 is fed in a step (2) to a distillation column K2a which is operated with rectifying section and stripping section and is equipped with a falling-film evaporator and separated bottom, and also column internals having structured packing which generate 10 theoretical plates. Column K2a is operated at the top with a direct condenser which consists of a column section equipped with structured packing and having a total collecting cup, pumped circuit and external heat exchanger. The column K2a is operated at an absolute top pressure of 2.0 bar, top temperature 288 K and bottom draw temperature 363 K.

Via the top of column K2a is obtained stream 9 which, as described at the outset, is metered into the reactor R1 as a recycle stream. The reflux ratio at the top of the column K2a is adjusted in such a way that stream 9 contains approx. 100 ppm of 2M3BN.

Via the bottom of the column K2a are obtained 59 kg/h of a stream 1b which contains 2.9% BD, 4.6% C2BU, 67% pentenenitriles, and also additionally the catalyst constituents. In relation to BD. C2BU is distinctly enriched compared to the feed.

Within step (2), stream 1b is conducted into a distillation column K2b which is operated in stripping mode and is equipped with falling-film evaporator, top condenser with postcondenser and also column internals having structured packing which generate 10 theoretical plates. The column is operated at an absolute top pressure of 150 mbar, top temperature 329 K and bottom draw temperature 373 K. The vapor stream of the column is partly condensed at 308 K and treated with a postcondenser at 263 K. The BD stream 2c, thus depleted of 2M3BN and other pentenenitriles, is compressed in a compressor V2 to an absolute pressure of 1.2 bar. The compressed gas stream is condensed at 279 K for the most part to obtain a stream 2e (5 kg/h), and a substream 2d (47 l (STP)/h, containing 44% C2BU) is disposed of in gaseous form. Stream 2e is recycled in liquid form into the condensate collecting vessel of the column K2a.

In a gaseous side draw of the column K2b, stream 11 is obtained (40 kg/h) and contains approx. 100 ppm of BD, 46% 2M3BN and 48% T3PN, and also, to a smaller extent. E2M2BN and Z2M2BN in addition to other pentenenitrile isomers. The position of the side draw is selected in such a way that the component 2M3BN in the stream 10 obtained via the bottom is depleted in relation to T3PN in a stripping section below the side draw.

Into column K2b are conducted 13 kg/h of a catalyst stream which is obtained as described in Example 1 of the German patent application having the title "Preparation of dinitriles" to BASF AG (B03/0525) as the side draw of the column K4 from step (4), containing a total of 73% pentenenitriles, 0.5% Ni(0), 18% ligand mixture and approx. 5% ADN.

Via the bottom of the column K2b is obtained the catalyst stream 10 containing 0.5% Ni(0), approx. 100 ppm of 2M3BN and 73% remaining pentenenitriles. Stream 10 is split into substream 10a (21 kg/h) which is recycled into the reactor R1. The other portion (10b) (5.4 kg/h) is fed to a regeneration according to DE-A-103 51 002, in order, after regeneration, to be used, for example, in the hydrocyanation of 3-pentenenitrile as described in Example 1 of DE-A-102 004 004 683.

In a step (3), stream 11 is conducted to a distillation column K3 which is equipped with circulation evaporator and top condenser, and also with structured packing which generate 30 theoretical plates. The column K3 is operated at an absolute top pressure of 180 mbar, top temperature 345 K and bottom draw temperature 363 K.

Into the column K3 are conducted 39 kg/h of recycle stream 5 from column K5 in step (5), containing 54% T3PN, 23% 2M3BN and 16% Z2M2BN, and also, in small amounts, further pentenenitrile isomers.

Via the top of column K3 are obtained 40 kg/h of a stream 13 containing 10% T3PN, 68% 2M3BN, 16% Z2M2BN, and also a total of 0.1% BD and C2BU and small amounts of other pentenenitrile isomers (T2PN, C2PN, C3PN, 4PN).

Via the bottom of column K3 are obtained 39 kg/h of stream 12 containing 97% in total of T3PN, C3PN and 4PN, and small amounts of other pentenenitrile isomers (T2PN, C2PN), and also approx. 100 ppm of 2M3BN and approx. 1% E2M2BN.

In Example 1, a catalyst system based on nickel(0) complexes with a mixture of ligands is used for the isomerization of 2M3BN to T3PN. The ligand mixture for the isomerization (referred to hereinbelow as isomerization ligand) comprises mixed phosphite ligands of the P(OR)(OR')(OR") class having randomly distributed R, R', R" from the group of m-tolyl, p-tolyl, o-isopropylphenyl, and approx. 40 mol % of the sum of the R, R', R" radicals are o-isopropylphenyl radicals. Such ligand mixtures are obtained in the reaction of a mixture of m- and p-cresol having a ratio of 2:1 of m-cresol compared to p-cresol and a stoichiometrically matched amount of o-isopropylphenol with a phosphorus trihalide.

In a step (4), stream 13 is conducted, together with a catalyst recycle stream 3a and a catalyst supplementation stream, into a reactor R2, designed as a tubular reactor, which is heated to 393 K. As the sum of recycled catalyst and fresh catalyst, 56 kg/h of a mixture having 20% T3PN, 5% 2M3BN and other pentenenitrile isomers, 55% isomerization ligand and 0.5% nickel(0), and also a small content of catalyst degradation products, is conducted into reactor R2.

As the product from reactor R2, 96 kg/h of stream 1 are obtained, containing 34% T3PN, 12.3% 2M3BN and small amounts of other pentenenitrile isomers (T2PN, C2PN, C3PN, 4PN), corresponding to a conversion of 60% 2M3BN.

In a step (5), stream 1 is conducted into a distillation column K5 which is operated as a rectifying column and is equipped with a falling-film evaporator, top condenser, reflux divider, gaseous side draw in the bottom region of the column, and also column internals with structured packing which generate 30 theoretical plates. The column is operated at an absolute top pressure of 250 mbar, top temperature 353 K and bottom draw temperature 373 K.

In column K5, the recovered catalyst stream 3 (56 kg/h) is obtained via the bottom, containing 20% T3PN in addition to other pentenenitriles, approx. 5% MGN and also 0.5% Ni(0) and 54% isomerization ligand. A small portion of stream 3 is discharged as stream 3b to restrict the accumulation of catalyst deactivation components and MGN. To supplement the amount of catalyst discharged, sufficient fresh catalyst containing 15% T3PN in addition to other pentenenitrile isomers, 1% Ni(0) and 80% isomerization ligand is metered in so that the Ni(0) content in the catalyst feed to reactor R2 is kept at 0.5%.

In column K5, a stream 4 is obtained via the top (0.8 kg/h), containing a total of 0.5% BD and C2BU, 50% 2M3BN, 41% Z2M2BN, and also small amounts of vinylcyclohexene (VCH) which is firstly present in traces in the BD starting material and secondly formed in small amounts in the hydrocyanation of butadiene, and ultimately accumulates in the 2M3BN cycle of the isomerization and has to be discharged together with 2M3BN, since the vapor pressures of 2M3BN and VCH are so close to one another that a separation by conventional distillation is not possible. The reflux ratio of column K5 is adjusted in such a way that 10 ppm of T3PN are present in stream 4. The draw rate of stream 4 from the top of column K5 is adjusted in such a way that 20% Z2M2BN and VCH are present in the top draw stream 13 of distillation column K3.

In column K5, a stream 5 is obtained via the gaseous side draw (39 kg/h) which, in addition to 3-pentenenitriles, comprises substantially the 2M3BN unconverted in the isomerization and, after condensation, is recycled in liquid form into column K3 as described above.

Example 2

Figure 4:
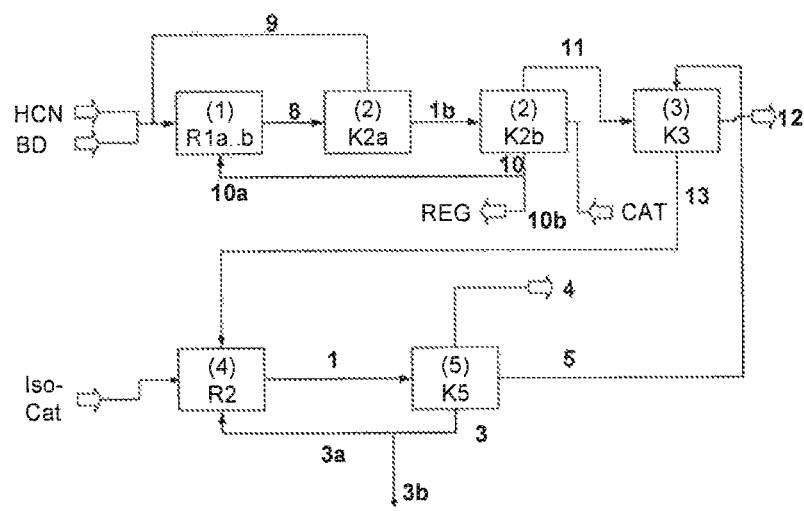
FIG. 4 is a schematic representation of Example 2.

Example 2 is illustrated with reference to FIG. 4.

In Example 2, a catalyst system based on nickel(0) complexes with chelatephosphite 2 as a ligand is used for the hydrocyanation of BD:

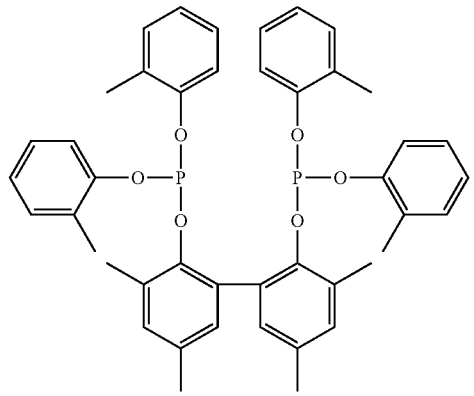

In a step (1), the following streams are conducted into a system composed of two reactors. R1a and R1b, each of capacity 12 l, each of which is equipped with a nozzle, impulse exchange tube, external pump circulation and in a heat exchanger disposed in the pump circulation system to remove the energy of reaction, and are heated to 363 K:

(1) 6 kg/h of liquid, unstabilized hydrogen cyanide freed of water by distillation to R1a,
(2) 6 kg/h of liquid, unstabilized hydrogen cyanide freed of water by distillation to R1b,
(3) 25 kg/h of BD to R1a, containing 0.25% C2BU, which has been treated by contact with alumina in order to remove water and TBP stabilizer,
(4) 2 kg/h of recycled BD from column K2a in step (2) to R1a (stream 9), so that the entire BD feed to reactor R1 obtained is a stream of 27 kg/h containing 98% BD and a total of 2% C2BU and 1-butene,
(5) 14 kg/h of nickel(0) catalyst solution to R1a, obtained as described below in this example as stream 10a from column K2b.

The stream 8 drawn off from reactor R1b (54 kg/h) contains a total of 4% BD and C2BU, corresponding to a conversion of 94% BD, and also a total of 74% pentenenitriles, of which 33% is T3PN, 37% 2M3BN and small amounts of Z2M2BN and E2M2BN, in addition to other pentenenitrile isomers, and also the catalyst constituents and catalyst degradation products and MGN.

In a step (2), stream 8 is had to a distillation column K2a which is operated as a rectifying column and is equipped with a falling-film evaporator, and also column internals having structured packing which generate 4 theoretical plates. Column K2a is operated at the top with a direct condenser which consists of a column section charged with random packing and having total collecting cup, pumped circulation and external heat exchanger. Column K2a is operated at an absolute top pressure of 0.8 bar, top temperature 263 K and bottom draw temperature 393 K.

Via the top of column K2a is obtained stream 9 which is metered into the reactor R1a as a recycle stream as described at the outset. The reflux ratio at the top of column K2a is adjusted in such a way that stream 9 contains 0.1% 2M3BN.

Via the bottom of column K2a are obtained 52 kg/h of a stream 1 b which contains 0.3% BD, 0.1% C2BU, 76% pentenenitriles and also additionally the catalyst constituents.

Within step (2), stream 1b is conducted into a distillation column K2b which is operated in stripping mode and is equipped with a falling-film evaporator, top condenser with postcondenser, and also column internals having structured packing which generate 4 theoretical plates. The column is operated at an absolute top pressure of 70 mbar, top temperature 333 K and bottom draw temperature 373 K.

At the gaseous side draw of column K2b, stream 11 is obtained (40 kg/h), containing 0.4% BD, 54% 2M3BN and 42% T3PN, and also, to a lesser extent, E2M2BN and Z2M2BN in addition to other pentenenitrile isomers.

Into column K2b are conducted 3 kg/h of a catalyst stream, containing a total of 45% pentenenitriles, 1.5% Ni(0) and the chelate ligand, obtained, for example, by reacting nickel(0)(cyclooctadienyl)$_2$ complex with the chelatephosphite 2.

Via the bottom of column K2b is obtained the catalyst stream 10, containing 1.2% Ni(0), 0.3% 2M3BN and 17% residual pentenenitriles. Stream 10 is partly recycled into reactor R1 (14 kg/h) (stream 10a). Another portion (stream 10b) (3.8 kg/h) is fed to a regeneration according to DE-A-103 51 002, in order to be used in the hydrocyanation of 3-pentenenitrile according to DE-A-102 004 004 683, or, if appropriate, recycled into the hydrocyanation of BD according to the process according to the invention.

In a step (3), stream 11 is conducted to a distillation column K3 which is equipped with circulation evaporator and top condenser, and also with structured packing which generate 45 theoretical plates. Column K3 is operated at an absolute top pressure of 1.0 bar, top temperature 395 K and bottom draw temperature 416 K.

In a step (5), 24 kg/h of recycle stream 5 from column K5 are conducted into column K3, containing 70% T3PN, 14% 2M3BN and 7% Z2M2BN, and also small amounts of further pentenenitrile isomers.

Via the top of column K3 are obtained 30 kg/h of a stream 13 containing 1% T3PN, 85% 2M3BN, 8% Z2M2BN, and also a total of 3% BD and C2BU in addition to other pentenenitrile isomers and VCH. The reflux ration of column K3 is adjusted in such a way that 1% T3PN is obtained overhead.

Via the bottom of column K3 are obtained 38 kg/h of stream 12 containing a total of 97% T3PN, C3PN and 4PN, and also approx. 10 ppm of 2M3BN and approx. 2% E2M2BN, and small amounts of MGN and also other pentenenitrile isomers.

In Example 2, the catalyst used for the isomerization is the chelatephosphite-based nickel(0) complex, as described for the hydrocyanation of BD in this example.

In a step (4), stream 13 is conducted, together with a catalyst recycle stream 3a and a catalyst supplementation stream, into a reactor R2, designed as a compartmented reactor having tubular characteristics and equipped with a preheater, by which the reaction mixture is heated to 383 K. As the sum of recycled catalyst and fresh catalyst, 12 kg/h of a mixture having 20% T3PN, 3% 2M3BN and other pentenenitrile isomers, 71% ligand mixture and 0.6% nickel (0), and also a small content of catalyst degradation products, are conducted into a reactor R2.

As the product from reactor R2, 43 kg/h of stream 1 are obtained, containing 53% T3PN, 12% 2M3BN, corresponding to a conversion of 80% 2M3BN.

In a step (5), stream 1 is conducted into a distillation column K5 which is equipped with a falling-film evaporator, top condenser, reflux divider, gaseous side draw in the bottom region of the column, and also column internals which generate 30 theoretical plates. The column is operated at an absolute top pressure of 377 mbar, top temperature 355 K and bottom draw temperature 368 K.

In column K5, the recovered catalyst stream 3 (11 kg/h) is obtained via the bottom, containing 20% T3PN in addition to other pentenenitriles, approx. 1% MGN, and also 0.6% Ni(0) and 54% ligand. A small portion (stream 3b) is discharged to restrict the accumulation of catalyst deactivation components and MGN. To replace the amount of catalyst discharged, sufficient fresh catalyst containing 40% pentenenitrile isomers, 1.2% Ni(0) and 55% ligand mixture is metered in so that the Ni(0) content in the catalyst feed to reactor R2 is kept at 0.6%.

In column K5, a stream 4 is obtained overhead (1.4 kg/h), containing a total of 18% BD and C2BU, 45% 2M3BN, 28% Z2M2BN, and also small amounts of vinylcyclohexene (VCH). The reflux ratio of column K5 is adjusted in such a way that 10 ppm of T3PN are present in stream 4. The draw rate of stream 4 from the top of column K8 is adjusted in such a way that 10% Z2M2BN and VCH are present in the top draw stream 13 of distillation column K3.

In column K5, a stream 5 is obtained via the gaseous side draw (24 kg/h) which, in addition to 3-pentenenitriles, comprises substantially the 2M3BN unconverted in the isomerization and after condensation, is recycled in liquid form into column K3 as described above.

Example 3

Figure 5:
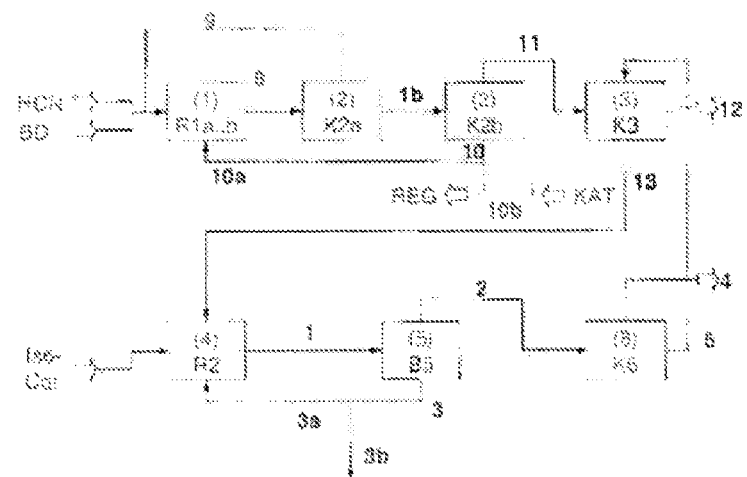
FIG. 5 is a schematic representation of Example 3.

Example 3 is illustrated with reference to FIG. 5.

In Example 3, a catalyst system based on nickel(0) complexes with a mixture of ligands is used for the hydrocyanation of butadiene. The ligand mixture for the hydrocyanation contains approx. 60 mol % of tri(m/p-tolyl) phosphite and 40 mol % of the chelate phosphite 2.

In a step (1), the following streams are conducted into a system composed of two reactors, R1a and R1b, each of capacity 12 l, each of which is equipped with a nozzle, impulse exchange tube, external pump circulation and in a heat exchanger disposed in the pump circulation system to remove the energy of reaction, and are heated to 363 K:

(1) 6 kg/h of liquid, unstabilized hydrogen cyanide freed of water by distillation to R1a,
(2) 6 kg/h of liquid, unstabilized hydrogen cyanide freed of water by distillation to R1b,
(3) 25 kg/h of commercial BD to R1a, containing 0.25% C2BU, which has been treated by contact with alumina in order to remove water and TBP stabilizer,
(4) 2 kg/h of recycled BD from column K2a in step (2) to R1a (stream 9), so that the entire BD feed to reactor R1 obtained is a stream of 27 kg/h containing 98% BD and a total of 2% C2BU and 1-butene,
(5) 14 kg/h of nickel(0) catalyst solution to R1a, obtained as described below in this example as stream 10a from column K2b.

The stream 8 drawn off from reactor R1b (54 kg/h) contains a total of 4% BD and C2BU, corresponding to a conversion of 94% BD, and also a total of 74% pentenenitriles, of which 33% is T3PN, 37% 2M3BN and small amounts of Z2M2BN and E2M2BN, other pentenenitrile isomers, and also the catalyst constituents and catalyst degradation products and MGN.

In a step (2), stream 8 is fed to a distillation column K2a which is operated as a rectifying column and is equipped with a falling-film evaporator, and also column internals having structured packing which generate 4 theoretical plates. Column K2a is operated at the top with a direct condenser which consists of a column section charged with random packing and having total collecting cup, pumped circulation and external heat exchanger. Column K2a is operated at an absolute top pressure of 0.8 bar, top temperature 263 K and bottom draw temperature 393 K.

Via the top of column K2a is obtained stream 9 which is metered into the reactor R1a as a recycle stream as described at the outset. The reflux ratio at the top of column K2a is adjusted in such a way that stream 9 contains 0.1% 2M3BN.

Via the bottom of column K2a are obtained 52 kg/h of a stream 1b which contains 0.3% BD, 0.1% C2BU, 76% pentenenitriles and also additionally the catalyst constituents.

Within step (2), stream 1b is conducted into a distillation column K2b which is operated in stripping mode and is equipped with a falling-film evaporator, top condenser with postcondenser, and also column internals having structured packing which generate 4 theoretical plates. The column is operated at an absolute top pressure of 70 mbar, top temperature 333 K and bottom draw temperature 373 K.

At the gaseous side draw of column K2b, stream 11 is obtained (40 kg/h), containing 0.4% BD, 54% 2M3BN and 42% T3PN, and also, to a lesser extent, E2M2BN and Z2M2BN in addition to other pentenenitrile isomers.

Into column K2b are conducted 5 kg/h of a catalyst stream which is obtained as described in Example 1 of the German patent application with the title "Preparation of dinitriles" to BASF AG (B03/0525) as the bottom draw of column K4 from step (4) of Example 2, containing a total of 45% pentenenitriles, 1.1% Ni(0), 38% ligand mixture and approx. 12% ADN.

Via the bottom of column K2b is obtained catalyst stream 10 containing 1.2% Ni(0), 0.3% 2M3BN and 17% residual pentenenitriles. Stream 10 is recycled partly into reactor R1 (14 kg/h) (stream 10a). Another portion (stream 10b) (3.8 kg/h) is fed to a regeneration according to DE-A-103 51 002, in order to be used in the hydrocyanation of 3-pentenenitrile according to DE-A-102 004 004 683.

In a step (3), stream 11 is conducted to a distillation column K3 which is equipped with circulation evaporator and top condenser, and also with structured packing which generate 45 theoretical plates. Column K3 is operated at an absolute top pressure of 1.0 bar, top temperature 395 K and bottom draw temperature 416 K.

In a step (6), 28 kg/h of recycle stream 5 from column K6 are conducted into column K3, containing 72% T3PN, 15% 2M3BN and 8% Z2M2BN, and also small amounts of further pentenenitrile isomers.

Via the top of column K3 are obtained 30 kg/h of a stream 13 containing 1% T3PN, 85% 2M3BN, 8% Z2M2BN, and also a total of 3% BD and C2BU, and further pentenenitrile isomers. The reflux ratio of column K3 is adjusted in such a way that 1% 3PN is obtained overhead.

Via the bottom of column K3 are obtained 38 kg/h of stream 12 containing a total of 97% T3PN, C3PN and 4PN, and also approx. 10 ppm of 2M3BN and approx. 2% E2M2BN, and small amounts of MGN and further pentenenitrile isomers.

In Example 3, a catalyst system based on nickel(0) complexes with a mixture of ligands is used for the isomerization of 2M3BN to T3PN. The ligand mixture for isomerization (referred to hereinbelow as isomerization ligand) comprises mixed phosphate ligands of the P(OR)(OR')(OR") class having randomly distributed R, R', R" from the group of phenyl, m-tolyl, p-tolyl, o-tolyl, at least 80 mol % of the sum of the R, R', R" radicals being m-tolyl and p-tolyl radicals. Such ligand mixtures are obtained in the reaction of a mixture of m- and p-cresol (having a mixing ratio of 2:1) of m-relative to p-cresol with a phosphorus trihalide. The promoter used for the isomerization reaction is zinc chloride, as described in U.S. Pat. No. 3,676,481, U.S. Pat. No. 3,852,329 and U.S. Pat. No. 4,298,546.

In a step (4), stream 13 is conducted, together with a catalyst recycle stream 3a and a catalyst supplementation stream, into a reactor R2, designed as a compartmented reactor having tubular characteristics and equipped with a preheater, by which the reaction mixture is heated to 383 K. As the sum of recycled catalyst and fresh catalyst, 12 kg/h of a mixture having 20% T3PN, 3% 2M3BN and other pentenenitrile isomers, 71% isomerization ligand and 0.6% nickel(0), and also a small content of catalyst degradation products, are conducted into reactor R2.

The product obtained from reactor R2 is 43 kg/h of stream 1 containing 53% T3PN, 12% 2M3BN, corresponding to a conversion of 80% 2M3BN.

In a step (5), stream 1 is conducted into an evaporator stage B5 which is equipped with forced circulation evaporator and top condenser. The evaporator stage B5 is operated at an absolute pressure of 510 mbar, bottom draw temperature 403 K and condensation temperature 366 K.

In evaporator stage B5, the recovered catalyst stream 3 (11 kg/h) is obtained via the bottom, containing 20% T3PN in addition to other pentenenitriles, approx. 10% MGN, and also 0.5% Ni(0) and 61% ligand mixture. A small portion (stream 3b) is discharged to restrict the accumulation of catalyst deactivation components and MGN. To replace the amount of catalyst discharged, sufficient fresh catalyst, containing approx. 15% pentenenitrile isomers, approx. 2.0% Ni(0), approx. 70% isomerization ligand and the zinc chloride promoter in a concentration which corresponds to a molar ratio of $ZnCl_2$ to nickel(0) of approx. 5, is metered in so that the Ni(0) content in the catalyst feed to reactor R2 is kept at 0.6%.

In the evaporator stage B5, stream 2 is obtained at the top condenser (25 kg/h), containing 1% BD, 68% T3PN, 16% 2M3BN and further pentenenitriles, and also small amounts of VCH.

In a step (6), stream 2 is conducted into distillation column K6 which is operated as a rectifying column and is equipped with a circulation evaporator, top condenser, and also column internals which generate 30 theoretical plates. The column is operated at an absolute top pressure of 340 mbar, top temperature 357 K, 313 K in the condenser and bottom draw temperature 373 K.

At the condenser of column K6, the gas phase obtained is approx. 100 l (STP)/h of a stream which consists substantially of BD.

In column K6, the liquid phase obtained at the top condenser is a stream 4 (1.1 kg/h), containing a total of 5% BD and C2BU, 50% 2M3BN, 30% Z2M2BN, and also small amounts of vinylcyclohexene (VCH). The reflux ratio of column K6 is adjusted in such a way that 1 ppm of T3PN is present in stream 4. The draw rate of stream 4 from the top of column K6 is adjusted in such a way that a total of 10% Z2M2BN and VCH are present in the feed to reactor R2.

In column K6, a stream 5 is obtained via the bottom (24 kg/h) which, in addition to 3-pentenenitriles, comprises substantially the 2M3BN unconverted in the isomerization, and is recycled into column K3 as described above.

Example 4

Figure 6:
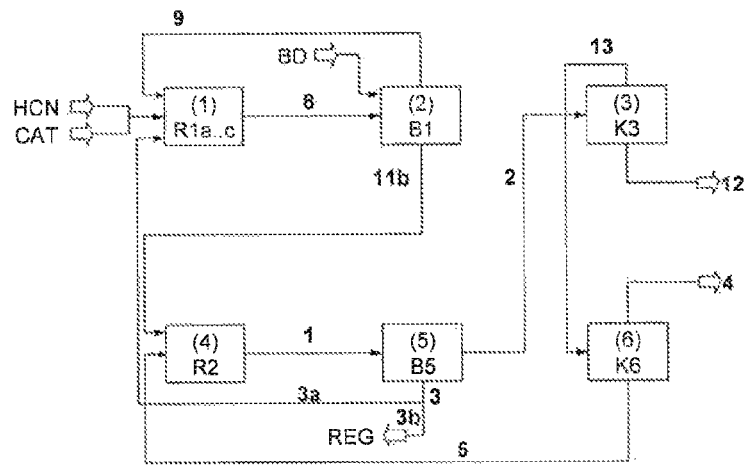
FIG. 6 is a schematic representation of Example 4.

Example 4 is illustrated with reference to FIG. 6.

In Example 3, a catalyst system based on nickel(0) complexes with a mixture of ligands is used for the hydrocyanation of butadiene. The ligand mixture for the hydrocyanation contains approx. 80 mol % of tri(m/p-tolyl) phosphite and 20 mol % of the chelatephosphite 2 (see Example 2).

In a step (1), the following streams are conducted into a system composed of three continuous stirred tanks R1a, R1b and R1c connected in series, each of capacity 10 l, which are heated to 373 K:

(1) 5.2 kg/h of liquid, unstabilized hydrogen cyanide freed of water by distillation to R1a,
(2) 4.0 kg/h of liquid, unstabilized hydrogen cyanide freed of water by distillation to R1b,
(3) 20 kg/h of 1 BD as stream 9 from the condenser of evaporator B1 in step (2), containing 92% BD, 2% T3PN, 4% 2M3BN and approx. 2% C2BU to R1a,
(4) 4.1 kg/h of nickel(0) catalyst solution to R1a, obtained as described below in this example, as stream 3a from evaporator stage B5 in step (5),
(5) 3.7 kg/h of nickel(0) catalyst solution to R1a, obtained as described in Example 3 of the German patent application with the title "Preparation of dinitriles" to BASF AG (B03/0525) as the bottom draw of column K4 from step (4) of Example 2, containing a total of 45% pentenenitriles, 1.1% Ni(0), 38% ligand mixture and approx. 12% ADN.

Reactor R1c is operated as a postreactor with the effluent from reactor R1b at 353 K.

Stream 8 drawn off from reactor R1c (37 kg/h) contains 1% BD, corresponding to a conversion of 98% BD, and also a total of 82% pentenenitriles, of which 36% is T3PN, 44% 2M3BN and small amounts of Z2M2BN and E2M2BN, and also the catalyst constituents and catalyst degradation products and MGN and further pentenenitrile isomers.

In a step (2), stream 8 is fed to an evaporator stage B1 which is equipped with a circulation evaporator. The evaporator stage B1 is operated at the top with a condenser which is flushed with condensed material from the reflux vessel. The evaporator stage B1 is operated at an absolute top pressure of 0.6 bar, condensation temperature 253 K and bottom draw temperature 363 K.

In the condensate collecting vessel of evaporator B1, 19.5 kg/h of commercial BD containing 0.25% C2BU are metered in, which have been treated by contact with molecular sieve, the water content of the BD used having been reduced to less than 10 ppm by weight of water.

From the condensate collecting vessel of evaporator stage B1, stream 9 is drawn off as the sum of recycled and freshly metered butadiene, and recycled to reactor R1a as described above.

Via the bottom of evaporator stage B1 are obtained 37 kg/h of a stream 11b which contains 1% BD, 82% pentenenitriles and also additionally the catalyst constituents.

In a step (4), stream 11b is conducted into a reactor R2, heated to 383 K and designed as a stirred tank with downstream delay section, and 2M3BN is isomerized to T3PN in the presence of the nickel catalyst.

A pentenenitrile recycle stream 5 is conducted into reactor R2 (10 kg/h) and is obtained in step (6) in column 6 as the bottom product containing 60% 2M3BN, a total of 10% T3PN with further pentenenitrile isomers, and also VCH and small amounts of BD.

From reactor R2, a stream 1 is obtained (45 kg/h) containing 62% T3PN and 14% 2M3BN, corresponding to a conversion of 70% 2M3BN to T3PN, and also the catalyst components.

In a step (5), stream 1 is conducted into an evaporator stage B5 which is equipped with a falling-film evaporator and condenser and is operated at an absolute pressure of 50 mbar and bottom draw temperature 393 K.

From the condenser of the evaporator stage B5, a stream 2 is obtained (38 kg/h), containing 91% pentenenitrile isomers and also approx. 1% BD and, to a lesser extent, E2M2BN, Z2M2BN and VCH.

Via the bottom of the evaporator stage B5, catalyst stream 3 is obtained (7.2 kg/h), containing 1.2% Ni(0), 0.1% 2M3BN and 15% residual pentenenitriles. Stream 3 is partly (stream 3a) recycled into reactor R1 (4.1 kg/h). The remainder (stream 3b) is fed to a regeneration according to DE-A-103 51 002, and can be used after the regeneration, for example, in a hydrocyanation of 3-pentenenitrile as in Example 2 of DE-A-102 004 004 683, or used again as the catalyst in the process according to the invention for hydrocyanating butadiene, if appropriate after removal of zinc chloride.

In a step (3), stream 2 is conducted to a distillation column K3 which is equipped with a forced circulation evaporator and top condenser, and also with column internals which generate 30 theoretical plates. Column K3 is operated at an absolute top pressure of 120 mbar, top temperature 334 K and bottom draw temperature 352 K.

Via the top of column K3 are obtained 10 kg/h of a stream 13 containing 5% T3PN, 60% 2M3BN, 4% Z2M2BN, and also a total of 4% BD and C2BU, and a remainder of predominantly VCH. The reflux ratio of column K3 is adjusted in such a way that 5% T3PN are obtained overhead.

Via the bottom of column K3 are obtained 27 kg/h of stream 12 containing a total of 98% T3PN, C3PN and 4PN, and also approx. 1000 ppm of 2M3BN and approx. 2% E2M2BN.

In a step (6) stream 13 is conducted into a distillation column K6 which is operated as a rectifying column and is equipped with a forced circulation evaporator, top condenser, reflux divider, and also column internals having structured packing which generate 15 theoretical plates. Column K6 is operated at an absolute top pressure of 380 mbar, top temperature 361 K and bottom draw temperature 365 K.

In column K6, a liquid stream 4 is obtained overhead (0.6 kg/h), containing a total of 4% BD and C2BU, 54% 2M3BN, 38% Z2M2BN, and also 2.5% vinylcyclohexene (VCH). The draw rate of stream 4 from the top of column K6 is adjusted in such a way that a total of 30% Z2M2BN and VCH are present in the top draw stream 13 of column K3. In column K6, a gaseous stream is obtained at the top condenser operated as a partial condenser (195 l (STP)/h) which comprises substantially BD.

In column K6, stream 5 is obtained via the bottom (9.4 kg/h) which, in addition to 3-pentenenitriles, comprises substantially the 2M3BN unconverted in the isomerization and is recycled into the isomerization reactor R2.

Example 5

Figure 7:
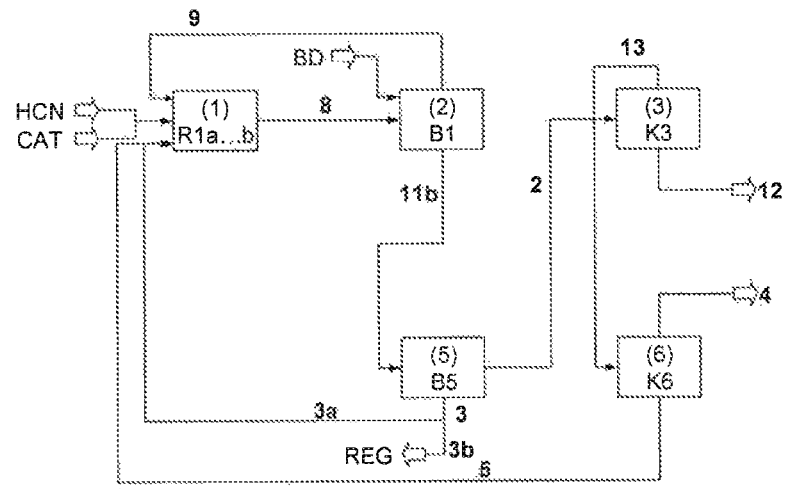
FIG. 7 is a schematic representation of Example 5.

Example 5 is illustrated with reference to FIG. 7.

In Example 5, a catalyst system based on nickel(0) complexes with a mixture of ligands is used for the hydrocyanation of BD. The ligand mixture for the hydrocyanation contains approx. 80 mol % of tri(m/p-tolyl) phosphite and 20 mol % of the chelate phosphonite 1 (see Example 1).

In a step (1), the following streams are conducted into a system composed of two continuous stirred tanks R1a and R1b connected in series, each of capacity 50 l, which are heated to 363 K:
- (1) 18 kg/h of liquid, unstabilized hydrogen cyanide freed of water by distillation in equal portions to reactors R1a and R1b,
- (2) 62 kg/h of BD as stream 9 from the top of evaporator B1 in step (2), containing 87% BD, 3% T3PN, 6% 2M3BN and approx. 2% C2BU to reactor R1a,
- (3) 61 kg/h of nickel(0) catalyst solution, obtained as described below in this example, as stream 3a from evaporator stage B5 in step (5) to reactor R1a,
- (4) 6.7 kg/h of nickel(0) catalyst solution to R1a, obtained as in Example 1 of the German patent application with the title "Preparation of dinitriles" to BASF AG (B03/0525) 1 as the bottom draw of column K4 from step (4) of Example 2, containing a total of 45% pentenenitriles, 1.1% Ni(0), 38% ligand mixture, and also approx. 12% ADN to reactor R1a, the butadiene stream and the catalyst stream being premixed before contacting with hydrogen cyanide.

The stream 8 drawn off from reactor R1b (177 kg/h) contains 11% BD, corresponding to a conversion of 66% BD, and also a total of 64% pentenenitriles, of which 32% is T3PN, 30% 2M3BN and small amounts of Z2M2BN and E2M2BN and further pentenenitrile isomers, and also the catalyst constituents and catalyst degradation products.

In a step (2), stream 8 is fed to an evaporator stage B1 which is equipped with a falling-film evaporator. The evaporator stage B1 is operated with a condenser at the top which is flushed with condensed material from the reflux vessel. The evaporator stage B1 is operated at an absolute top pressure of 1.3 bar, condensation temperature 278 K and bottom draw temperature 403 K.

Into the condensate collecting vessel of the evaporator stage B1 are metered 37 kg/h of commercial BD containing 0.25% C2BU which has been treated by contact with molecular sieve, the water content of the BD used having been removed to less than 5 ppm by weight of water and the TBP stabilizer present in the BD used reaching the condensate collecting vessel and condenser flushing circuit in concentrations on the ppm scale.

From the condensate collecting vessel of the evaporator stage B1, stream 9 is drawn off as the sum of recycled and freshly metered BD and recycled to reactor R1a as described above.

Via the bottom of evaporator stage B1 are obtained 152 kg/h of a stream 11b which contains 0.9% BD, 16% 2M3BN, 51% T3PN and further pentenenitrile isomers, and also additionally the catalyst constituents. The composition of the bottom effluent of the evaporator stage allows a degree of conversion of 50% 2M3BN to T3PN in the bottom of the evaporator B1 to be concluded.

In a step (5), stream 11b is conducted into an evaporator stage B5 which is equipped with falling-film evaporator and condenser and is operated at an absolute pressure of 260 mbar and bottom draw temperature 383 K.

From the evaporator stage B5, a stream 2 is obtained in gaseous form (83 kg/h), containing 9396 pentenenitrile isomers, and also approx. 1% BD and, to a lesser extent, E2M2BN, Z2M2BN and VCH. Stream 2 is conducted into distillation column K3 in step (3).

Via the bottom of evaporator stage B5 is obtained the catalyst stream 3 (69 kg/h), containing 0.6% Ni(0), 2% 2M3BN and 42% residual pentenenitriles. Stream 4 is for the most part recycled into reactor R1 (61.4 kg/h) (stream 3a). The remainder (stream 3b) is fed to a regeneration according to DE-A-103 51 002, and may be used, for example, in the hydrocyanation of 3-pentenenitrile, as described in Example 1 of DE-A-102 004 004 683.

In a step (3), stream 2 is conducted in gaseous form to a distillation column K3 which is equipped with a forced circulation-decompression evaporator and top condenser, and also with structured packing which generate 30 theoretical plates. Column K3 is operated at an absolute top pressure of 80 mbar, top temperature 375 K and bottom draw temperature 343 K.

Via the top of column K3 are obtained 36 kg/h of a stream 13 containing 15% T3PN, 64% 2M3BN, 3% Z2M2BN, and also a total of 4% BD and C2BU, the remainder comprising predominantly VCH. The reflux ratio of column K3 is adjusted in such a way that 15% T3PN is obtained overhead.

Via the bottom of column K3 are obtained 47 kg/h of stream 12 containing a total of 98% T3PN, C3PN and 4PN, and also 100 ppm of 2M3BN and approx. 1% E2M2BN.

In a step (6) stream 13 is conducted into a distillation column K6 which is operated as a rectifying column and is equipped with a forced circulation evaporator, top condenser, reflux divider, and also column internals having structured packing which generate 45 theoretical plates. The column is operated at an absolute top pressure of 320 mbar, condensation temperature 288 K and bottom draw temperature 363 K.

In column K6, a liquid stream 4 is obtained via the top (6.8 kg/h) containing a total of 10% BD and C2BU, 80% 2M3BN, 8% Z2M2BN, and also 0.5% vinylcyclohexene (VCH). The draw rate of stream 4 from the top of column K6 is adjusted in such a way that a total of 15% Z2M2BN and VCH is present in the top draw stream 3 of the column K3. In column K6, a gaseous stream is obtained at the top condenser operated as a partial condenser (263 l (STP)/h) which comprises substantially BD.

In column K6, stream 5 is obtained via the bottom (28.7 kg/h) which, in addition to 3-pentenenitriles, comprises substantially the 2M3BN unconverted in the isomerization and is recycled into the hydrocyanation reactor R1.

Example 6

Figure 8:
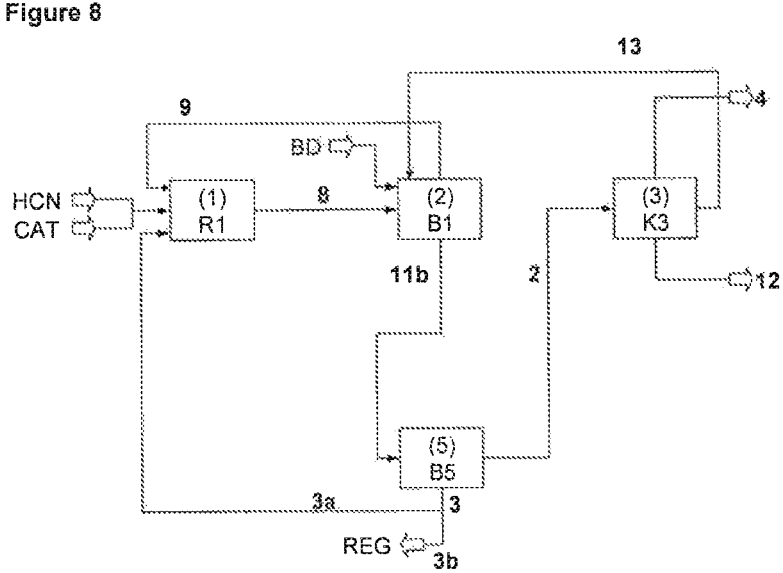
FIG. 8 is a schematic representation of Example 6.

Example 6 is illustrated with reference to FIG. 8,

In Example 8, a catalyst system based on nickel(0) complexes with chelate phosphonite 1 as the ligand is used for the hydrocyanation of BD (see Example 1).

In a step (1), the following streams are conducted into a continuously operated stirred tank R1 of volume 30 l which is heated to 363 K:
- (1) 16 kg/h of liquid, unstabilized hydrogen cyanide freed of water by distillation,
- (2) 55 kg/h of BD as stream 9 from the top of evaporator B1 in step (2), containing 87% BD, 3% T3PN, 6% 2M3BN and approx. 2% C2BU,
- (3) 10 kg/h of nickel(0) catalyst solution, obtained as described below in this example as stream 3a from evaporator stage B5 in step (5), containing a total of 42% pentenenitriles, 23% ligand, 0.9% nickel(0), and also in each case approx. 10% ADN and MGN, (4) 4 kg/h of nickel(0) catalyst solution to R1, containing a total of 45% pentenenitriles, 1.5% Ni(0) and 48% ligand.

The stream 8 drawn off from reactor R1 (89 kg/h) contains 17% BD, corresponding to a conversion of 71% BD, and also a total of 73% pentenenitriles, of which 32% is T3PN, 36% 2M3BN and small amounts of Z2M2BN and E2M2BN, and also the catalyst constituents and the catalyst degradation products.

In a step (2), stream 8 is fed to an evaporator stage B1 which is equipped with a falling-film evaporator. The evaporator stage B1 is operated with a condenser at the top which is flushed with condensed material from the reflux vessel. The evaporator stage B1 is operated at an absolute top pressure of 1.3 bar, condensation temperature 278 K and bottom draw temperature 403 K.

Into the condensate collecting vessel of evaporator stage B1 are metered 34 kg/h of commercial BD containing 0.25% C2BU, which have been treated by contact with alumina, the water content of BD used having been reduced to less than 10 ppm by weight of water and the TBP content to less than 10 ppm.

From the condensate collecting vessel of the evaporator stage, stream 9 is drawn off as the sum of recycled and freshly metered butadiene, and recycled to reactor R1a as described above.

Via the bottom of evaporator stage B1 are obtained 76 kg/h of a stream 5 which contains 0.8% BD, 12% 2M3BN, 69% T3PN and further pentenenitrile isomers, and also additionally the catalyst constituents. The composition of the bottom effluent of the evaporator stage corresponds to a degree of conversion of 75% 2M3BN to T3PN in the bottom of the evaporator stage B1.

In a step (5), stream 5 is conducted into an evaporator stage B5 which is equipped with a falling-film evaporator and condenser and is operated at an absolute pressure of 220 mbar and bottom draw temperature 381 K.

From the evaporator stage B5, a stream 2 is obtained in gaseous form (58 kg/h) containing 97% pentenenitrile isomers, and also approx. 1% BD and, to a lesser extent, E2M2BN, Z2M2BN and VCH.

Via the bottom of the evaporator stage B5 is obtained the catalyst stream 3 (17 kg/h) containing 0.9% Ni(0), 0.3% 2M3BN and 42% residual pentenenitriles. Stream 3 is for the most part recycled into reactor R1 (10 kg/h) (stream 3a). The remainder (stream 3b) is fed to a regeneration according to US 2003/0100442 and may, after the regeneration, be used in a hydrocyanation of 3-pentenenitrile or recycled into the process according to the invention, into the step for hydrocyanating BD.

Stream 2 is condensed and, in a step 3, conducted in liquid form to a distillation column K3 which is equipped with a forced circulation evaporator and top condenser, and also with structured packing which generate 50 theoretical plates. Column K3 is operated at an absolute top pressure of 200 mbar, top temperature 342 K and bottom draw temperature 366 K.

At the top of column K3, a stream 4 is obtained, containing 10% BD, 18% Z2M2BN, 68% 2M3BN, and also further pentenenitrile isomers and VCH. The reflux ratio of column K3 is adjusted in such a way that the top draw stream contains 18% Z2M2BN.

At a liquid side draw of column K3, 8 kg/h of a stream 13 are obtained, containing 0.5% T3PN, 85% 2M3BN, 5% Z2M2BN, 10% BD. Stream 13 is recycled into evaporator stage B1.

Via the bottom of column K3 are obtained 47 kg/h of stream 12 containing a total of 98% T3PN, C3PN and 4PN, and also 100 ppm of 2M3BN and approx. 1% E2M2BN.

What is claimed is:

1. A process for preparing 3-pentenenitrile comprising the following process steps:
    (a) isomerizing a reactant stream which comprises 2-methyl-3-butenenitrile over at least one dissolved or dispersed isomerization catalyst to give a stream 1 that comprises the at least one isomerization catalyst, 2-methyl-3-butenenitrile, 3-pentenenitrile and (Z)-2-methyl-2-butenenitrile,
    (b) distilling stream 1 to obtain a stream 2 top product that comprises 2-methyl-3-butenenitrile, 3-pentenenitrile and (Z)-2-methyl-2-butenenitrile, and a stream 3 bottom product that comprises the at least one isomerization catalyst, wherein a pressure and temperature conditions in process step (b) are 1 mbar to 6 bar, and 40 to 180° C. at the bottom of the distillation apparatus,
    (c) distilling stream 2 at a bottom temperature of 40 to 180° C. and a pressure of 10 mbar to 500 mbar to obtain a stream 4 top product which, compared to stream 2 is enriched in (Z)-2-methyl-2-butenenitrile, based on the sum of all pentenenitriles in stream 2,
    hydrocyanating 1,3-butadiene over at least one hydrocyanation catalyst using hydrogen cyanide to obtain a stream 8 which comprises the at least one hydrocyanation catalyst, 3-pentenenitrile, 2-methyl-3-butenenitrile, 1,3-butadiene and residues of hydrogen cyanide,
    distilling stream 8 one or more times to obtain a stream 9 which comprises 1,3-butadiene, a stream 10 which comprises the at least one hydrocyanation catalyst, and a stream 11 which comprises 3-pentenenitrile and 2-methyl-3-butenenitrile, and
    distilling stream 11 to obtain a stream 12 bottom product which comprises 3-pentenenitrile, wherein the distilling of the stream 11 is carried out in the step (c) distillation column almong with stream 2 from process step (b) to provide the stream 4 as top product comprising (Z)-2-methyl-2-butenenitrile, stream 12 as bottom product comprising 3-pentenenitrile, and stream 13 as a side draw stream comprising 2-methyl-3-butenenitrile, which is recycled to the reactant stream of step (a).

2. The process according to claim 1, wherein the at least one isomerization catalyst obtained in stream 3 in process step (b) is recycled to process step (a).

3. The process according to claim 1, wherein process steps (b) and (c) are carried out together in one distillation apparatus, in which case stream 3 which comprises the at least one isomerization catalyst is obtained as the bottom product, stream 4 which comprises (Z)-2-methyl-2-butenenitrile as the top product, and stream 5 which comprises 3-pentenenitrile and 2-methyl-3-butenenitrile at a side draw of the column.

4. The process according to claim 1, wherein process steps (a), (b) and (c) are carried out together in one distillation apparatus, in which case stream 4 which comprises (Z)-2-methyl-2-butenenitrile is obtained as the top product, and stream 5 which comprises 3-pentenenitrile and 2-methyl-3-butenenitrile at a side draw of the distillation apparatus, and the isomerization catalyst remains in the bottom of the distillation column.

5. The process according to claim 1, wherein the isomerization catalyst contains nickel, a trivalent phosphorus-containing compound which as a ligand complexes the nickel, and optionally, a Lewis acid.

6. The process according to claim 1, wherein the hydrocyanation catalyst and the isomerization catalyst are identical.

7. The process according to claim 5, wherein the trivalent phosphorus-containing compound is of formula (Ib)

$$P(O-R^1)_x(O-R^2)_y(O-R^3)_z(O-R^4)_p \qquad (Ib)$$

where
- $R^1$: is an aromatic radical having a $C_1$-$C_{18}$-alkyl substituent in the o-position to the oxygen atom, or having an aromatic substituent in the o-position to the oxygen atom, or having a fused aromatic system in the o-position to the oxygen atom,
- $R^2$: is an aromatic radical having a $C_1$-$C_{18}$-alkyl substituent in the imposition to the oxygen atom, or having an aromatic substituent in the m-position to the oxygen atom, or having a fused aromatic system in the m-position to the oxygen atom, the aromatic radical bearing a hydrogen atom in the o-position to the oxygen atom,
- $R^3$: is an aromatic radical having a $C_1$-$C_{18}$-alkyl substituent in the p-position to the oxygen atom, or having an aromatic substituent in the p-position to the oxygen atom, the aromatic radical bearing a hydrogen atom in the o-position to the oxygen,
- $R^4$: is an aromatic radical which bears substituents other than those defined for $R^1$, $R^2$ and $R^3$ in the o-, m- and p-position to the oxygen atom, the aromatic radical bearing a hydrogen atom in the o-position to the oxygen atom,
- x: is 1 or 2, and
- y, z, p: are each independently 0, 1 or 2, with the proviso that x+y+z+p=3.

8. The process according to claim 5, wherein the trivalent phosphorus-containing compound is of formula (Ib)

$$P(O-R^1)_x(O-R^2)_y(O-R^3)_z(O-R^4)_p \qquad (Ib)$$

where $R^1$, $R^2$ and $R^3$ are each independently selected from o-isopropylphenyl, m-tolyl and p-tolyl, and $R^4$ is phenyl; x is 1 or 2, and y, z, p are each independently 0, 1 or 2, with the proviso that x+y+z+p=3; and mixtures thereof.

9. The process according to claim 1, wherein step (c) is carried out at a temperature of 5 to 150° C. at the top of the distillation apparatus.

10. The process according to claim 1, wherein step (c) is carried out at a temperature of 60 to 140° C. at the bottom of the distillation apparatus.

11. The process according to claim 1, wherein the stream 12 as bottom product comprises a single isomer of 3-pentenenitrile or a mixture of two, three, four or five different such isomers including cis-2-pentenenitrile, trans-2-pentenenitrile, cis-3-pentenenitrile, trans-3-pentenenitrile, or 4-pentenenitrile.

* * * * *